United States Patent
Parton et al.

(10) Patent No.: US 12,325,687 B2
(45) Date of Patent: Jun. 10, 2025

(54) PROCESS FOR THE CONVERSION OF FURFURYL ALCOHOL INTO A LEVULINATE ESTER

(71) Applicant: GFBiochemicals IP Assets B.V., Geleen (NL)

(72) Inventors: Rudy Parton, Geleen (NL); Arie De Rijke, Geleen (NL)

(73) Assignee: GFBIOCHEMICALS IP ASSETS B.V., Geleen (NL)

( * ) Notice: Subject to any disclaimer, the term of this patent is extended or adjusted under 35 U.S.C. 154(b) by 304 days.

(21) Appl. No.: 18/041,272

(22) PCT Filed: Aug. 14, 2021

(86) PCT No.: PCT/EP2021/072657
§ 371 (c)(1),
(2) Date: Feb. 10, 2023

(87) PCT Pub. No.: WO2022/034235
PCT Pub. Date: Feb. 17, 2022

(65) Prior Publication Data
US 2023/0322655 A1    Oct. 12, 2023

(30) Foreign Application Priority Data
Aug. 14, 2020   (EP) .................................... 20191220

(51) Int. Cl.
*C07C 67/40*   (2006.01)
*C07C 67/00*   (2006.01)
(52) U.S. Cl.
CPC .............. *C07C 67/40* (2013.01); *C07C 67/00* (2013.01)

(58) Field of Classification Search
CPC ........ C07C 67/00; C07C 67/40; C07C 69/716
See application file for complete search history.

(56) References Cited

U.S. PATENT DOCUMENTS

| | | | |
|---|---|---|---|
| 2,738,367 A * | 3/1956 | Redmon ................. | C07C 51/00 562/537 |
| 2,917,537 A * | 12/1959 | Haury ..................... | C07C 67/00 560/174 |
| 10,590,060 B2 * | 3/2020 | Chappaz ................. | C07C 67/29 |

OTHER PUBLICATIONS

Hengne, A. M., Single pot conversion of furfural alcohol to levulinic esters and gamma-valerolactone in the presence of sulfonic acid functionalized ILs and metal catalyst., Green Chemistry, The Journal of the Royal Society of Chemistry, 2013, vol. 15, pp. 2540-2547 (Year: 2013).*

Garcia-Suarez et al. "Pd-catalysed formation of ester products from cascade reaction of 5-hydroxymethylfurfural with 1-hexene", Applied Catalysis A, General 569, Jan. 2019, pp. 170-174.

(Continued)

*Primary Examiner* — Yate' K Cutliff
(74) *Attorney, Agent, or Firm* — Haukaas Fortius PLLC; Michael Haukaas

(57) ABSTRACT

The invention relates to a process for the conversion of furfuryl alcohol into a levulinate ester comprising contacting furfuryl alcohol; an alcohol, or a mixture thereof; and a homogeneous catalyst at a first reaction temperature in the range of from 125 to 180° C. to form a reaction mixture; and forming the levulinate ester in the reaction mixture, characterised in that the first homogeneous catalyst is a sulfonic acid catalyst.

20 Claims, 4 Drawing Sheets

(56) References Cited

OTHER PUBLICATIONS

Hengne et al., "Single pot conversion of furfuryl alcohol to levulinic esters and γ-valerolactone in the presence of sulfonic acid functionalized ILs and metal catalysts", Green Chem. 2013, Jul. 12, 2013, 15, pp. 2540-2547.
International Search Report and Written Opinion of the ISA/EP dated Dec. 22, 2021 in International Application No. PCT/EP2021/072657, 8pgs.
Yang et al., "Hydrothermal carbon enriched with sulfonic and carboxyl groups as an efficient solid acid catalyst for butanolysis of furfuryl alcohol", Catalysis Communications 123, Feb. 19, 2019, pp. 109-113.

\* cited by examiner

PROCESS FOR THE CONVERSION OF FURFURYL ALCOHOL INTO A LEVULINATE ESTER

RELATED APPLICATIONS

This application is a National Stage filing under 35 U.S.C. § 371 of International Application No. PCT/EP2021/072657 filed Aug. 14, 2021, which claims priority to European Patent Application No. 20191220.1 filed Aug. 14, 2020, which applications are incorporated herein by reference.

FIELD OF THE INVENTION

The present invention provides a process for the conversion of furfuryl alcohol into a levulinate ester with a low production of an ether byproduct, such as dialkyl ether.

BACKGROUND OF THE INVENTION

The production of levulinic acid or levulinate esters from furfuryl alcohol with an alcohol in the presence of an acidic catalyst is generally known.

For example, U.S. Pat. No. 2,738,367 discloses a process in which furfuryl alcohol, at a temperature between 30 and 100° C., is converted to levulinic acid in water by strong acidic ion exchange resins which are both in large excess compared to the amount of furfuryl alcohol. The catalysts that are disclosed in U.S. Pat. No. 2,738,367 are the heterogeneous cation exchange resins marketed under the tradenames "Amberlite IR-120" and "Amberlite IR-105". The reaction is carried out by the slow addition of furfuryl alcohol to the reaction mixture and, after feeding of the furfuryl alcohol, the reaction is continued in a batch mode under the same reaction conditions. The disadvantage of the method is that the heterogeneous catalyst deactivates.

PCT patent publication WO 2010/102203 (International Patent Application No. PCT/US2010/026358) (to Segetis) discloses a method in which a mixture 2 containing furfuryl alcohol and an alkanol is added to a mixture 1 containing the alkanol, alkyl levulinate, from levulinic acid and the same alkanol, and a protic acid catalyst. The protic acid catalyst is disclosed as being a strong protic acid catalyst selected from "hydrochloric acid, hydrobromic acid, hydriodic acid, sulfuric acid, pyrosulfuric acid, perchloric acid, a phenylsulfonic acid, methanesulfonic acid, trifluoromethanesulfonic acid, p-toluenesulfonic acid, 1-napthalenesulfonic acid, 2-napthalene sulfonic acid, chlorosulfonic acid, fluorosulfonic acid, and the like"; an alkyl-aromatic sulfonic acid, an aromatic sulfonic acid, or an aliphatic sulfonic acid; or a weak protic acid selected from phosphoric acid, pyrophosphoric acid, polyphosphoric acid, sulfamic acid, alkali metal salts of sulfuric acid such as sodium hydrogen sulfate or potassium hydrogen sulfate, chloric acid, bromic acid, perbromic acid, iodic acid, and periodic acid. However, only examples with sulfuric acid as homogeneous catalysts are taught.

PCT patent publication WO 2007/023173 discloses a process in which a strong porous acid ion-exchange resin is used as a heterogeneous catalyst to convert furfuryl alcohol with either water or alkyl alcohol to levulinic acid or alkyl levulinates, respectively. The life time of the catalyst is increased compared to gel type acid ion-exchange resins. Again, however, the heterogeneous catalyst will deactivate. To suppress undesired diethyl ether production, Lange at al (ChemSusChem, Wiley-VCH Verlag, Weinheim; www.chemsuschem.org), 2009, 2, pp 437-441 "Conversion of Furfuryl Alcohol Into Ethyl Levulinate Using Solid Acid Catalysts") suggest using a porous heterogeneous catalyst comprising strong acid ion-exchange resin, wherein the catalyst has pores with an average pore diameter in the range of from 1 to 1000 nm, such as a macro-reticular ion-exchange resin. Lange et al and WO2007/023173 (hereinafter Lange et al 2009) investigate different heterogeneous acids, as well as sulfuric acid, as catalysts for the conversion of furfuryl alcohol to ethyl levulinate. They found out that all heterogeneous catalysts were less active than sulfuric acid per acid site (being the strongest acid) (see FIG. 5), except Amberlyst 46 which follows the performance of sulfuric acid itself. Since Amberlyst 46 is a resin containing benzene sulfonic acid groups which are more weakly acidic than sulfuric acid, acid strength seems therefore not critical for yield of ethyl levulinate under the tested reaction conditions. However, Amberlyst 46 is mainly surface sulfonated, while the other tested resins have also internally sulfonic acid groups. Therefore, accessibility seems to be important for having a high yield of ethyl levulinate under the tested reaction conditions and, under identical conditions, the source of the acid is not important for the yield, as long as the acid sites are easily accessible. Based on those results, the skilled person would expect homogeneous sulfonic acids to give an identical yield as sulfuric acid itself when the same amount of acidic protons are added via the catalyst. Furthermore, Lange et al 2009 showed that, at high yield of ethyl levulinate (surpassing 84% yield), the yield of diethyl ether increases rapidly—over 3 mol % based on ethanol for sulfuric acid (so over 8 mol % based on furfuryl alcohol) and even higher for sulfonic acid containing resins (combination of FIGS. 5 and 6). Based on these results, the skilled person will not expect that homogeneous sulfonic acids would be associated with an improved yield of alkyl levulinates and, at the same time, a low production of dialkyl ether.

There are a limited number of articles available about homogeneous catalysts for the conversion of furfuryl alcohol with alkanols to alkyl levulinates and still less using homogeneous sulfonic acids.

One article which uses sulfuric acid as a homogeneous catalyst is Peng et al. (Facile and Efficient Conversion of Furfuryl Alcohol into n-Butyl Levulinate Catalyzed by Extremely Low Acid Concentration, BioResources 2014 9(3), 3825-3834). They used a batch process with concentrations of sulfuric acid between 0.01 and 1 wt %, reflecting the low acid concentrations in the title to this article. The yields were slightly above 80% and the best, and identical, yields were obtained at 110 and 120° C. reaction temperature. Yields of up to 97% were obtained, but that was with 1 wt % concentration of furfuryl alcohol (a more than 100 fold molar excess of butanol in a batch reaction that is not suitable for economical production). They did not perform a comparison with other homogeneous catalysts, such as homogeneous sulfonic acids, but nothing in their work showed that sulfuric acid is not the catalyst of choice to make n-butyl levulinate.

In another article from Zhou et al. (Ethane-Bridged Organosilica Nanotubes Functionalized with Arenesulfonic Acid and Phenyl Groups for the Efficient Conversion of Levulinic Acid or Furfuryl Alcohol to Ethyl Levulinate Chem. Cat. Chem. 2016 (8) 2037-2048), the ethanolysis of furfuryl alcohol is studied on silicas which are functionalized with sulfonic acid groups and the performance is compared to Amberlyst 15 and sulfuric acid. In this case, higher yields were obtained with the Amberlyst-15 than with sulfuric acid, but the turnover frequency per acid site is only slightly higher than sulfuric acid and the silicas functionalized with sulfonic acid groups performed the best. No homogeneous sulfonic acids were used.

Para-toluene sulfonic acid (p-TSA) is used as a reference material to compare the performance of sulfonated graphene oxides with homogeneous catalysts such as sulfuric acid and p-TSA (Zhu, Chen, Xue, Wu, Wang, and Fan, "Graphene Oxide: An Efficient Acid Catalyst for Alcoholysis and Esterification Reactions", ChemCatChem Communications (Wiley-VCH Verlag, Weinheim), 2014, 6, 3080-3083, see Table 1 entries 17 and 18). The reaction was performed in batch reaction at 80° C. They used in weight a more than 20 times excess of aliphatic alcohol compared to furfuryl alcohol. With pTSA, they obtained 94.6% of ethyl levulinate (EL) and 0.6 wt % ethyl methylfurylether (EMF, an intermediate) and 0.5 wt % of triethoxypentanone (TEP, another intermediate). So that would give, after all intermediates are converted, about 95.6 wt % ethyl levulinate (TEP has a higher molecular weight than EL so the 1.1 wt % of TEP gives less than 1 wt % of EL). In the case of sulfuric acid, 92.5 wt % of ethyl levulinate is obtained with 1.7 wt % EMF and 0.1 wt % of TEP. With sulfuric acid, 10 times less catalyst was used, that may be the reason why the yield was slightly lower. Because less catalyst was used, the reaction went more slowly and more intermediates are not yet converted to the levulinates. That would give about 94.2-94.3 wt % of ethyl levulinate, if all intermediates are converted. Essentially both final values of ethyl levulinate are very similar because of the limited accuracy of the catalytic and analysis methods. Indeed, very low amounts of substrate are used (0.4 g of furfuryl alcohol in an overall mixture of 10 g which is mainly ethanol and reflects the uneconomically high ratio of ethanol over furfuryl alcohol) and no internal standards were added to the reaction or used in the GC Method. Therefore, they have had to assume that all products are seen in the GC, which obviously is not the case for the heavies made. So the final yield is certainly an over-estimation of the real yield and the yields for pTSA and sulfuric acid in Table 1 are essentially similar. The conditions (batch, high amounts of catalyst compared to furfuryl alcohol (FFOH/p-TSA=4 g/g and 0.67 g/g/hour, FFOH/$H_2SO_4$=40 g/g and 6.67 g/g/hour), high amounts of alcohol compared to furfuryl alcohol (EtOH/FFOH=24 g/g or 51 mol/mol)) are very different from our conditions (fed-batch or continuous, FFOH/p-TSA=optionally <200 g/g/hour; optionally >2 g/g/hr, further optionally >5 g/g/hour, still further optionally >10 g/g/hour), a molar ratio of EtOH/FFOH between about 1:1 and 5:1). Zhu et al does not provide any evidence for a significantly better performance of p-TSA than sulfuric acid, possibly due to the low reaction temperatures they use. At an equivalent amount of graphene oxide (0.1 g), they obtained 95.5% of ethyl levulinate (EL) and 0.3 wt % ethyl methylfurylether (EMF, an intermediate) and 0.1 wt % of triethoxypentanone (TEP, another intermediate). Zhu et al conclude that graphene oxide is "a highly active, selective, and reusable acid catalyst for the production of alkyl levulinates".

Under essentially similar conditions, Rode et al. (Hengne, Kamble and Rode, "Single pot conversion of furfuryl alcohol to levulinic esters and γ-valerolactone in the presence of sulfonic acid functionalized ILs and metal catalysts", Green Chemistry (The Royal Society of Chemistry), 2013, 15, 2540-2547) found with sulfuric acid (0.3 g), 5 g furfuryl alcohol (FFOH/cat=16.667 g/g or 8.333 g/g/hour, methanol 95 ml (molar ratio MeOH/FFOH=46:1, 130° C., 2 hour reaction time), 68% conversion with 74% selectivity to methyl levulinate, 16% to methyl furfuryl ether and 10% other products (see entry 2 of Table 1). Rode et al focuses on sulfonic acid-functionalised ionic liquids (denoted $SO_3H$-ILs), and carbon supported Ru, Re, Ir and Ag catalysts. With an ionic catalyst liquid [BMIm-SH] [HSO4] (1-Butyl sulfonic acid, 3-methyl imidazolium hydrogen sulfate ionic liquid), derived from BMIm-SH and pTSA and comprising the MIm cation and a p-TSA anion, a conversion of 95% was obtained with 76% methyl levulinate, 11% methyl furfuryl ether and 13% other products (see entry 12 of Table 1). Obviously, an ionic liquid of pTSA, being a salt of pTSA that is prepared by reacting pTSA—an acid—with a base, is not the same as pTSA. The ionic liquid with sulfuric acid gave 99% conversion with 95% methyl levulinate, 2% methyl furfuryl ether and 3% other products (see entry 13 of Table 1). In an ionic setting, sulfuric acid performed slightly better than pTSA (see entries 13 and 12 of Table 1, carried out at 130° C.). So, no indication was found that p-TSA can perform better than sulfuric acid, but ionic liquids are, of course, other molecules. No homogeneous sulfonic acids, as defined herein, are used to convert furfuryl alcohol to levulinates. Table 1 describes the different catalysts used in Rode. As can be seen from Table 1, sulfuric acid is used as homogeneous acid and 4 heterogeneous acids (Amberlyst-15, SO4-ZrO2, 20% DTP-SiO2 20% DTP-MMT), the other catalysts being ionic liquids with methylimidazole, NMP and BMIm-SH as bases and sulfuric acid, pTSA, trifluoric acid and chlorosulfonic acid as the acid part of the salt.

Ionic liquids are salts that, as salts, have totally different properties than the acid and bases from which they are made. Ionic Liquids are a new class of purely ionic, salt-like materials that are liquid at unusually low temperatures. Currently, it's "official" definition uses the boiling point of water as a point of reference: "These are ionic compounds which are liquid below 100° C." More commonly, These have melting points below room temperature; some of them even have melting points below 0° C. These new materials are liquid over a wide temperature range (300-400° C.) from the melting point to the decomposition temperature of these compounds. If we were to compare a typical ionic liquid, e.g., 1-ethyl-3-methylimidazolium ethylsulfate (m.p. <−20° C.), with a typical inorganic salt, e.g., table salt (NaCl, m.p. 801° C.), it becomes obvious why there is a difference. The ionic liquid has a significantly lower symmetry! Furthermore, the charge of the cation as well as the charge of the anion is distributed over a larger volume of the molecule by resonance. As a consequence, the solidification of the ionic liquid will take place at lower temperatures. In some cases, especially if long aliphatic side chains are involved, a glass transition is observed instead of a melting point.

In the article of Rode, ionic liquids with acidic properties are used but, as said, an ionic liquid with pTSA has different properties than pTSA. So it is not possible to extrapolate results of BMIm-SH/pTSA to pTSA or vice versa.

The behaviour of the ionic liquids as catalyst is different from the behavior of pTSA herein. Rode found "However, alkyl levulinate selectivity was found to decrease from 99 to 85% with an increase in alcohol chain length from ethanol to n-butanol." see page 2542 below FIG. 2. In contrast, we find comparable yields for ethanol and butanol.

p-TSA was heterogenized via reaction with glucose and acrylic acid under hydrothermal conditions (Yang, Zhang, Ao and Zhang, "Hydrothermal Carbon Enriched with Sulfonic and carboxyl groups as an efficient solid acid catalyst for butanolysis of furfuryl alcohol", Catalysis Communications (Elsevier) 123 (2019) 109-113). The heterogeneous catalyst obtained was compared with p-TSA for the reaction between furfuryl alcohol and butanol. At 120° C., 0.196 g furfuryl alcohol, 5.92 g butanol (molar ratio ButOH/FFOH=40:1), 0.1 g catalyst (FFOH/p-TSA=2 g/g or 0.5 g/g/hour; 4 h reaction), a conversion of 100% is obtained with a yield for butyl levulinate of 75% and 3.6% butyl furfuryl ether (Table 2, entry 5). Under these conditions, 16% of humins (heavies) are made, see Table S2, entry 5. At a lower temperature (80° C.), the conversion was still 100%, but now 94.2 wt % of butyl levulinate was obtained with 1.5% butyl furfuryl ether (Table 2, entry 5b). Under these conditions, 2.5% of humins (heavies) are made, see Table S2, entry 5b. Based on those results, the skilled person would work with heterogenized p-TSA at temperatures below 100° C.

The conversion of furfuryl alcohol with water to levulinic acid gave lower yield with p-toluene sulfonic acid as catalyst than with most of the heterogeneous catalysts tested in the article (An, Song, Sun, Zhang, Zhang, and Guo, "Conversion of Furfuryl Alcohol to Levulinic Acid in Aqueous Solution Catalyzed by Shell Thickness-Controlled Arenesulfonic Acid Functionalized Ethyl-Bridged Organosilica Hollow Nanospheres" ACS Sustainable Chem. Eng. 2018, 6, 3, 3113-3123) and the TOF (Turn-Over Frequency) was by far the lowest for p-TSA (FIGS. 8 a and b). The authors say (page 3120): "As shown in FIG. 8a, the LA yield rapidly increases at the beginning of p-toluenesulfonic acid-catalyzed FAL hydrolysis reaction, and the yield reaches to 31.5% after the reaction proceeds for 30 min. However, the increase of the LA yield becomes gradually slow as further increasing the reaction time, and the yield is 46.0% over period of 120 min." The authors say also (page 3120): "Both p-toluenesulfonic acid and Amberlyst-15 are super strong Brönsted acid with extremely high acid site density (6846 and 4800 μeq g$^{-1}$), which can ensure them significantly high reaction rate at the initial stage of FAL hydrolysis to LA. However, their super strong Brönsted acid nature can also facilitate FAL polymerization in current reaction system, leading to unwanted brownish-black oligomers or humins (FIGS. S2 and S3, and Scheme 1). Accordingly, the selectivity of p-toluenesulfonic acid or Amberlyst-15 to LA decreases as the reaction goes on, accompanied with the slowly increased or even decreased LA yield." That is confirmed in the literature because it is found that p-TSA is an efficient catalyst for the polymerization of furfuryl alcohol (article 1: M. Principe, P. Ortiz, R. Martinez, "An NMR study of poly(furfuryl alcohol) prepared with p-toluenesulphonic acid", Polym. Int. 48 (1999) 637-641 and article 2: Martha Principe, Ricardo Martínez, Pedro Ortiz and Jacques Rieumont, "The Polymerization of Furfuryl Alcohol with p-toluenesulfonic Acid: Photocross-Linkeable Feature of the Polymer Polimeros": Ciência e Tecnologia, vol. 10, n° 1, p. 8-14, 2000). Based on these articles, the skilled person has no incentive to choose a homogeneous catalyst such as p-TSA as catalyst because oligomerization is expected as an important side reaction and yields were relatively low.

Previous methods all produce ether, such as dialkylether as a byproduct, although often not identified as such. It is hypothesised that the ether is not only reducing the recovery yield of the alcohol, which is used in excess and, therefore, for economic reasons, needs to be recycled, but also forms a safety issue in the plant because the alcohol is often recovered via distillation and the ether will be automatically recycled together with the alcohol and will be built up in the process. Moreover, the ethers, such as dialkyl ethers, have low auto ignition temperatures (diethyl and dibutyl ethers respectively 160 and 175° C.), so they create a potential safety problem which needs to be borne in mind in both plant operations and plant construction.

Yang et al (Catalysis Communications, 123 (2019), pp 109-112) concerns hydrothermal carbon enriched with sulfonic and carboxyl groups as a solid acid catalyst for butanolysis of furfuryl alcohol. Entry 5 of Table 2 compares the Yang catalysts with pTSA in a Parr batch reactor under reaction conditions comprising 0.196 FAL, 5.92 g n-butanol, 0.1 g catalyst, 120° C. and 4 hours. Table 2 reports a 75% yield of butyl levulinate and 3.6% butoxymethylfuran (BMF) at 120° C. The remainder of the 100% conversion is not identified (other than up to 16.0% humins, with reference to Table S2). Entry 5 of Table 2 provides further yields at 80° C.—94.2% and 1.5%, respectively—thus the butyl levulinate yield falls as the temperature rises to 120° C. Thus, in Yang's Table 2, pTSA is used at 2 different temperatures—120° C. and 80° C. Both temperatures give complete conversion under the Yang conditions but, at 80° C. the yield and therefore selectivity (94.2%) was significantly higher than at 120° C. (75%). In Yang, the ratio of furfuryl alcohol/pTSA=0.196 g/0.1 g=1.92 while, herein, the catalyst is between 0.1 and 5 wt % of the total reaction mixture and the molar ratios of alcohol/furfuryl alcohol is between 1/1 and 5/1. So, even with 5/1 and 5 wt % catalyst, there still is at least 3 times more furfuryl alcohol than catalyst. More optimal conditions herein would be 1 wt % catalyst and an alcohol/furfuryl alcohol ration of 2; in which case, the ratio of furfuryl alcohol/catalyst is close to 33. Finally, from Yang, the skilled person expects to find the optimal temperature at a lower temperature then 120° C. and not at the higher reaction temperatures claimed herein.

Garcia-Suarez et al (Applied Catalysis A, General, 569 (2019), pp 170-174) concerns Pd-catalysis of certain ester products. Table 2, entry 1 uses furfuryl alcohol as the substrate. The catalysts are Pd(OAc)$_2$ at 0.025 mmol, DTBPMB (1,2-bis(di-tert-butylphosphinomethyl)benzene) ligand (0.125 mmol), and MSA (methanesulfonic acid) at 1 mmol. The remaining reaction conditions are substrate (1 mmol), 1-hexene (1.8 mmol) and MeOH (5 mL) at a reaction temperature of 120 C for 20 hours. While the conversion of furfuryl alcohol is >99%, the yield is 19.3% (methyl heptanoate (MH), 21.4% methyl levulinate (ML) and 19.5% gamma-valerolactone (GVL). The remainder of the >99% conversion is not identified. There is an equal amount of catalyst (1 mmol) used as furfuryl alcohol (1 mmol) and the amount of methanol (5 ml) is in huge excess as it is about 200 mmol (MW=32 and density 0.792 g/ml). Moreover the selectivity of 21.4+19.5=40.9% of good product of the acid conversion of furfuryl alcohol is rather low. The 19.3% of methyl heptanoate originates from the reaction of 1-hexene with carbon monoxide coming from furfuryl alcohol. So, at least 19.3% of the furfuryl alcohol is decomposed to generate that carbon monoxide, because entry 6 shows that the methyl levulinate is NOT able to generate carbon monoxide. So, based on this experiment and combined with Yang, mentioned above, the skilled person would not convert furfuryl alcohol with pTSA at 120° C., but would, instead, use a lower temperature such as 80° C. Of course the low yield of good acid decomposition product in entry 1 Table 2 is likely to be the result of the co-presence of Pd in the reaction, but it would not encourage the skilled person to perform the reaction without Pd at 120° C.

It is an object of the present invention to optimise levulinate ester yield, while minimising the production of ether byproducts.

SUMMARY OF THE INVENTION

It has now been found that homogeneous sulfonic acids have a surprisingly better yield than sulfuric acid in the conversion of furfuryl alcohol with alcohols to levulinate esters above 125° C.

According to the invention, there is provided a process for the conversion of furfuryl alcohol into a levulinate ester, the process comprising contacting furfuryl alcohol; an alcohol or a mixture thereof; and a homogeneous catalyst at a first reaction temperature in the range of from about 125 to about 180° C. to form a reaction mixture; and forming the levulinate ester in the reaction mixture, characterised in that the first homogeneous catalyst is a sulfonic acid catalyst.

Optionally, the first homogeneous catalyst consists of the sulfonic acid catalyst. In other words, no other homogeneous or heterogeneous catalyst is present.

Optionally, the reaction is carried out at temperatures between about 125 or 130 and 170° C., about 125 or 130 and 160° C., about 125 or 130 and about 150° C., further optionally about 140° C.

Optionally, the sulfonic acid catalyst is selected from the group consisting of an alkyl-aromatic sulfonic acid, an aromatic sulfonic acid, a halosulfonic acid, and an aliphatic sulfonic acid; optionally, the sulfonic acid catalyst is p-toluenesulfonic acid or its monohydrate, 7,7-dimethyl-2-oxobicyclo[2.2.1]heptan-1-yl)methanesulfonic acid (camphor sulfonic acid) or methanesulfonic acid; or hydrates of each thereof. Salts of sulfonic acid catalysts are excluded.

Optionally, the sulfonic acid catalyst is an alkyl-aromatic sulfonic acid or an aromatic sulfonic acid selected from the group consisting of phenylsulfonic acid, p-toluenesulfonic acid, dodecyl benzene sulfonic acid, 1-napthalenesulfonic acid, and 2-napthalene sulfonic acid; or the sulfonic acid catalyst is an aliphatic sulfonic acid, optionally a straight chain, branched or cyclic alkyl sulfonic acid, such as methanesulfonic acid, trifluoromethanesulfonic acid, octanesulfonic acid, perfluorooctanesulfonic acid, and 7,7-dimethyl-2-oxobicyclo[2.2.1]heptan-1-yl)methanesulfonic acid (camphor sulfonic acid); or the halosulfonic acid is selected from chlorosulfonic acid, 3-chloromethanesulfonic acid, 3-fluoromethanesulfonic acid and fluorosulfonic acid; or hydrates of each thereof. Salts of such sulfonic acid catalysts are excluded.

Further optionally, the sulfonic acid catalyst is p-toluenesulfonic acid or p-toluenesulfonic acid monohydrate; or camphor sulfonic acid or camphor sulfonic acid monohydrate; or methanesulfonic acid or its hydrate.

The sulfonic acid catalyst, used in the present invention, is not a sulfonic acid-functionalised ionic liquid.

Optionally, the sulfonic acid catalyst comprises about 0.1 to about 5% (w/w), about 0.1 to about 3 (w/w) optionally about 0.5 to about 3% (w/w); further optionally about 0.5 to about 1.5% (w/w), still optionally about 1% (w/w), of the reaction mixture; and/or wherein the molar ratio of the alcohol to the furfuryl alcohol added to the reaction mixture is between about 1:1 to 5:1, optionally about 1.1:1 and 3:1; further optionally between about 1.2:1 and 2.7:1; still further optionally about 2.2:1 or about 1.5:1; and/or wherein the furfuryl alcohol is fed into the reaction mixture at a feed rate of no more than 200 grams furfuryl alcohol per gram of the catalyst in the reaction mixture per hour, optionally no more than 100 g/g/h, more optionally no more than 50 g/g/h.

Optionally, the alcohol is a primary or secondary alcohol selected from a C1-24 straight or branched chain alcohol; further optionally selected from methanol, ethanol, n-propanol, isopropanol, n-butanol, isobutanol, 2-butanol, n-pentanol, isopentanol, n-hexanol, n-octanol, n-decanol or 2-ethylhexan-1-ol; or an alkoxy-alkanol, optionally an alkoxyethanol such as β-methoxy ethanol or β-ethoxyethanol; or a combination of two or more thereof.

Alternatively, the alcohol is selected from an alicyclic alcohol optionally selected from cyclohexanol, cyclopentanol, tetrahydrofurfuryl alcohol, and 5-methyl-2-(propan-2-yl)cyclohexan-1-ol; or an unsaturated aliphatic alcohol optionally selected from prop-2-ene-1-ol, 3,7-dimethylocta-2,6-dien-1-ol and prop-2-yn-1-ol; or a glycol that is a primary alcohol optionally selected from ethylene glycol, 1,3-propanediol, and 1-4-butanediol; or a combination of two or more thereof.

Further alternatively, the alcohol is a mixture of one or more primary and secondary alcohols; and/or one or more alicyclic alcohols; and/or one or more unsaturated aliphatic alcohols; optionally selected from fusel alcohols and Guerbet alcohols; and one or more glycols.

Optionally, the process is carried out either in a fed-batch mode; or in a CSTR (continuous stirred tank reactor) optionally followed by a PFR (plug flow reactor).

Optionally, the contacting is carried out in a fed batch reactor.

When carried out in fed batch mode, the reaction mixture may formed by providing (i) a first mixture comprising the alcohol or a mixture thereof, and, optionally, the homogeneous sulfonic acid catalyst in the fed batch reactor; continuously or discontinuously feeding (ii) a second mixture comprising the furfuryl alcohol, and an additional amount of the alcohol or a mixture thereof to (i) the first mixture in the fed batch reactor; and continuously or discontinuously feeding to the fed batch reactor, separately from the second mixture, a third mixture comprising either (iii) an additional amount of the homogeneous sulfonic acid catalyst if the first mixture comprises the homogeneous sulfonic acid catalyst; or the homogeneous sulfonic acid catalyst if the first mixture does not comprise the homogeneous sulfonic acid catalyst.

Optionally, the third mixture is fed continuously or discontinuously to the fed batch reactor, separately from the second mixture and beginning at the same time as continuous or discontinuous feeding of the second mixture. The third mixture may be fed to the fed batch reactor after the second mixture is continuously or discontinuously fed to the fed batch reactor. However, you would not want to wait too long because, if the catalyst concentration in the fed batch reactor falls too low, the furfuryl alcohol concentration rises in the fed batch reactor and that will have a negative effect on the yield.

When the process is carried out in fed batch mode, optionally, the first mixture is heated to the first reaction temperature before the second mixture, and the third mixture are mixed with the first mixture. Further optionally, the alcohol is heated to the first reaction temperature before the catalyst is added to form the first mixture. Alternatively or additionally, the alcohol may be heated above the boiling point of the alcohol.

When the process is carried out in fed batch mode, the first temperature may maintained for up to about 2 hours, optionally about 5 to 60 minutes, after mixing the second mixture with the first mixture has been completed; or, alternatively, the first temperature is raised to a second reaction temperature after mixing the second mixture with the first mixture has been completed. Optionally, the reaction mixture is maintained at the second reaction temperature for between 5 and 120 minutes.

Alternatively, the process is continuous and is carried out in a continuous stirred-tank reactor. Optionally, a number of CSTRs are in series, from which, further optionally, the first CSTR runs at at least 90% conversion of furfuryl alcohol.

When the process is carried out in continuous mode, the continuous stirred-tank reactor may be filled with the reaction mixture by providing (i) a first mixture comprising the alcohol or a mixture thereof, and, optionally, the homogeneous sulfonic acid catalyst in the reactor; continuously or discontinuously feeding (ii) a second mixture comprising the furfuryl alcohol, and an additional amount of the alcohol or a mixture thereof to (i) the first mixture in the reactor; and continuously or discontinuously feeding to the reactor, separately from the second mixture, a third mixture comprising either (iii) an additional amount of the homogeneous sulfonic acid catalyst if the first mixture comprises the homogeneous sulfonic acid catalyst; or the homogeneous sulfonic acid catalyst if the first mixture does not comprise the homogeneous sulfonic acid catalyst.

Optionally, the third mixture is fed continuously or discontinuously to the continuous stirred-tank reactor, separately from the second mixture and beginning at the same time as continuous or discontinuous feeding of the second mixture. The third mixture may be fed to the continuous stirred-tank reactor after the second mixture is continuously or discontinuously fed to the continuous stirred-tank reactor. However, you would not want to wait too long because, if the catalyst concentration in the reactor falls too low, the furfuryl alcohol concentration rises in the reactor and that will have a negative effect on the yield.

When the process is carried out in continuous mode, the first mixture is heated to the first reaction temperature before the second mixture, and the third mixture are mixed with the first mixture.

When the process is carried out in continuous mode, the sulfonic acid catalyst is selected such that the sulfonic acid catalyst comprises about 0.1 to about 5% (w/w), optionally about 0.5 to about 3% (w/w); further optionally about 0.5 to about 1.5% (w/w), still optionally about 1% (w/w), of the reaction mixture.

Optionally, and irrespective of whether the process is carried out in fed batch or continuous mode, the second mixture is added to the reaction mixture at a feed rate of no more than 200 grams furfuryl alcohol per gram of the catalyst in the reaction mixture per hour, optionally no more than 100 g/g/h, more optionally no more than 50 g/g/h.

Optionally, alternatively or additionally, and irrespective of whether the process is carried out in fed batch or continuous mode, the second mixture is mixed with the reaction mixture at a feed rate of at least 2 grams furfuryl alcohol per gram of the catalyst in the reaction mixture per hour, optionally at least 5 g/g/hour, further optionally at least 10 g/g/hour, still further optionally at least 20 g/g/h.

Optionally, and irrespective of whether the process is carried out in fed batch or continuous mode, the first and second mixtures comprise, in total, a molar ratio of the alkyl alcohol to the furfuryl alcohol of between about 1:1 to 5:1, optionally about 1.1:1 and 3:1; further optionally between about 1.2:1 and 2.7:1; still further optionally about 2.2:1 or about 1.5:1.

Optionally, and irrespective of whether the process is carried out in fed batch or continuous mode, the molar ratio of the alcohol to the furfuryl alcohol in the reaction mixture is at least 20:1, optionally at least 50:1, further optionally at least 100:1, still further optionally at least 200:1.

When the process is carried out in continuous mode, when the continuous stirred-tank reactor has been filled to a desired volume, a volume of the reaction mixture is withdrawn from the continuous stirred-tank reactor; and the desired volume is replenished by continuously or discontinuously feeding the second mixture to the reactor; and, separately, continuously or discontinuously feeding the third mixture to the reactor, wherein the withdrawn volume is, optionally, fed to a second reactor, optionally, plug flow reactor, a second CSTR or a fed-batch reactor that is in series with the continuous stirred-tank reactor. Thus, continuous feeding of the second mixture and the third mixture continues and, at the same time, an identical volume as the total of both mixtures together is continuously discharged from the CSTR to a second reactor, optionally to a plug flow reactor, a second CSTR or a fed-batch reactor. In fact, continuously feeding and discharging is the definition of a CSTR, such that, when the continuous stirred-tank reactor has been filled to a desired volume, the overall system changes from fed-batch to CSTR mode of operation.

Optionally if the process is carried out fed-batch or in a CSTR followed by a second reactor such as 1 or more CSTR's or by a PFR, then, after the first reactor, a higher temperature can be applied in one or more of the second reactors.

Optionally, the withdrawn volume is fed to a second rector, such as a plug flow reactor, that is in series with the continuous stirred-tank reactor and the process is carried out in the second reactor at a second reaction temperature, the second reaction temperature being the same as, or 5 to 15° C. higher than, the first reaction temperature in the continuous stirred-tank reactor; and/or the residence time in the second reactor is in the range of 5 to 120 minutes, optionally about 10 to 60 minutes.

Optionally, the reaction mixture is maintained at atmospheric pressure or, if the reactor is enclosed, at autogenic pressure (for example, at an elevated pressure of up to 10 bar for methanol). Further optionally, the reaction mixture is maintained under autogenic pressure (i.e., pressure that is not applied externally but, simply, derives from the closed nature of the container and the $\rho$, P, T) relationship for the fluid (its equation of state).

Optionally, the reaction mixture is maintained at the first reaction temperature without further addition of furfuryl alcohol, until the concentration of furfuryl alcohol is below 1% (w/w), optionally, below 0.5 % (w/w), further optionally, below 0.25% (w/w), still further optionally below 0.01% (w/w) based on the total weight of the reaction mixture. Optionally or additionally, the rate of addition is as such that the furfuryl alcohol concentration in the reactor alcohol is below 1% (w/w), optionally, below 0.5% (w/w), further optionally, below 0.25% (w/w), still further optionally below 0.01% (w/w) based on the total weight of the reaction mixture.

Optionally, the process further comprises collecting the levulinate ester formed, wherein the collecting comprises evaporation of alcohol, distillation of the levulinate ester; recovery or neutralisation and removal of the catalyst; decanting of soluble from insoluble reaction products, filtration of insoluble from soluble reaction products, liquid-liquid extraction, or a combination thereof; wherein, further optionally, the distillation comprises vacuum distillation, wiped film evaporation or falling film evaporation. Still further optionally, the collecting is carried out in two steps, wherein a first step comprises evaporation of the alcohol and a second step comprises evaporation of the levulinate ester; or wherein a first step comprises evaporation of the alcohol and a first portion of the levulinate ester, and a second step comprises removal of a second portion of the levulinate ester.

Optionally, a byproduct comprising levulinic acid is esterified to form levulinate ester.

Optionally, at the end of a reaction according to the process of the present invention, and prior to purification of the reaction products thereof, a crude reacted mixture contains at least about 70 mole percent yield of levulinate ester based on furfuryl alcohol. In some embodiments, a crude reacted mixture contains at least about 80 mole percent of levulinate ester based on furfuryl alcohol. In some embodiments, the crude reacted mixture contains up to about 85 mole percent yield of levulinate ester based on furfuryl alcohol. In some embodiments, the crude reacted mixture contains up to about 90 mole percent yield of levulinate ester based on furfuryl alcohol.

Optionally, at the end of a reaction according to the process of the present invention, and prior to purification of the reaction products thereof, a crude reacted mixture contains up to about 70 mole percent yield of total levulinates (i.e. levulinate ester plus levulinic acid) based on furfuryl alcohol. In some embodiments, the crude reacted mixture contains up to about 80 mole percent yield of total levulinates (i.e. levulinate ester plus levulinic acid) based on furfuryl alcohol. In some embodiments, the crude reacted mixture contains up to about 85 mole percent yield of total levulinates (i.e. levulinate ester plus levulinic acid) based on furfuryl alcohol. In some embodiments, the crude reacted mixture contains up to about 90 mole percent yield of total levulinates (i.e. levulinate ester plus levulinic acid) based on furfuryl alcohol. In some embodiments, the crude reacted mixture contains up to about 95 mole percent yield of total levulinates (i.e. levulinate ester plus levulinic acid) based on furfuryl alcohol. In some embodiments, soluble materials in the crude reacted mixture contain no furfuryl alcohol, only alkanol, levulinic acid, dialkyl ether and levulinate ester and very small amounts of heavies and other byproducts (for example, dimers of furfuryl alcohol, aldol condensates of levulinate ester) as determined by analytical methods such as proton NMR, HPLC, or GC/MS.

Optionally, at the end of a reaction according to the process of the present invention, and prior to/or after purification of the reaction products thereof, an observable byproduct of the reaction is a tarry or oily residue, which is, in embodiments, about 20% or less by weight of furfuryl alcohol added. In some embodiments the tarry or oily residue is 10% or less by weight of furfuryl alcohol added. In some embodiments the tarry or oily residue is 5% or less by weight of furfuryl alcohol added. The content of the tarry/oily residue is measured by evaporating alkanol and levulinate ester and weighing the remaining materials or an aliquot thereof from the reaction vessel.

Optionally, at the end of a reaction according to the process of the present invention, and prior to purification of the reaction products thereof, a crude reacted mixture contains no more than 8 mol % of ethers based on furfuryl alcohol which is freshly made in 1 pass and is added to the recycled amount of di alkyl ether which was already present in the feed. In some embodiments, a crude reacted mixture makes in 1 pass no more than about 5 mole percent of ethers based on furfuryl alcohol. In some embodiments, the crude reacted mixture makes in 1 pass no more than about 2 mole percent yield of ethers based on furfuryl alcohol. In some embodiments, the crude reacted mixture makes no more than about 1 mole percent yield of ethers based on furfuryl alcohol. The dialkylether will be recycled with the excess of alcohol so, what is important, is the amount made in 1 pass in the reactor. The amount of dialkyl ether in the recycled alcohol is controlled via a purge stream so that the process is operated safely.

Under the reaction conditions of a process according to the present invention, a higher yield of levulinate ester is obtained and less ether is made than with the industrial homogeneous inorganic acids such as sulfuric acid.

Furthermore, homogeneous sulfonic acid catalysts are inexpensive, compared to the heterogeneous acid catalysts, and do not deactivate as readily, again compared to the heterogeneous acid catalysts, which deactivate by deposition of heavies and often cannot be recycled in an economic manner. The homogeneous acid catalysts are often used in amounts 1 to 20 times lower than the heterogeneous catalysts. So the higher productivity, lower amount and lower economic cost of the homogeneous catalyst does not makes it worthwhile to recycle them after reaction and they are often inactivated via neutralization with a base.

For example, about 5-10 g of product per g of heterogeneous catalyst after which the catalyst could not be recycled anymore. Herein, for example, more than 50 g of product per g of catalyst can be made and as already mentioned, the homogeneous catalyst is also less costly than the heterogeneous catalyst.

DETAILED DESCRIPTION OF THE INVENTION

In the process according to the invention, in order to obtain a higher yield of levulinate ester with less ether byproduct, it is important is that the concentration of furfuryl alcohol is always low and the alcohol/furfuryl alcohol molar ratio is always high. That can be achieved either by:

1. a fed-batch reactor. In this case, at least part of the alcohol and optionally at least part of the sulfonic acid homogeneous catalyst is loaded in the reactor and a mixture of furfuryl alcohol with, optionally, alcohol is fed at the same time to the reactor. Optionally part of the sulfonic acid homogeneous catalyst is fed also in a separate feeding line to the reactor.
2. A CSTR which runs at at least 90% conversion of furfuryl alcohol, more preferably 95% conversion more preferably 98% conversion, in which the furfuryl alcohol and the homogeneous catalyst are separately fed to the CSTR and the molar ratio of alcohol/furfuryl alcohol is between 1:1 and 5:1, more preferably between 1.2:1 and 3:1, more preferably between 1.5:1 and 2.7:1. The CSTR may be followed by a second CSTR, or multiple CSTR's in series, or by a PFR (plug flow reactor or a tube).

Preferably, the conversion reaction is carried out in liquid phase. An advantage of a liquid phase reaction is that liquid by-products that may be formed, such as, for example, oligomeric condensation products of furfuryl alcohol and/or levulinate ester, will stay in solution. Therefore, preferably a liquid reaction mixture comprising furfuryl alcohol and alcohol is contacted with the first homogeneous catalyst.

In order to limit the amount of by-products (in particular oligomeric condensation products of furfuryl alcohol) formed in the contacting step of claim 1 herein, the concentration of furfuryl alcohol is kept below 1 wt %, preferably below 0.5 wt %, based on the total weight of the reaction mixture. Typically, the concentration of furfuryl alcohol in the first CSTR, or in the reactor of the fed-batch set-up, is below 0.1 wt %, preferably below 0.01 wt %. The concentration has to be low enough to avoid polymerization of furfuryl alcohol (must be below 1 wt %) but also has to be high enough so as to get a good reaction rate.

A low concentration of furfuryl alcohol in the reaction mixture may be achieved in several ways. The reaction mixture may, for example, be diluted with an excess of the other reactant, i.e. the alcohol, or with the reaction product, i.e. levulinate ester, or with a diluent not being reactant or reaction product, for example sulfolane, gamma valerolactone or a carboxylate ester. Alternatively or additionally, staged supply of furfuryl alcohol to the reaction mixture, or a continuously stirred tank reactor (CSTR) operating at high conversion may be applied, in order to keep the concentration of furfuryl alcohol, in the reaction mixture, sufficiently low.

The reaction mixture may be maintained in contact at the first reaction temperature in the range of from 125 to 180° C. with the first homogeneous catalyst, without further addition of furfuryl alcohol to the reaction mixture, until the concentration of furfuryl alcohol is below 0.01 wt %, more preferably below 0.005 wt %, even more preferably below 0.001 wt %, each based on the total weight of the reaction mixture.

In order to achieve a high conversion of furfuryl alcohol with high selectivity, the alcohol is present in the reaction mixture in stoichiometric excess. Therefore, the molar ratio of the alcohol(s) and furfuryl alcohol in the reaction mixture is at least 20:1, more preferably at least 50:1, even more preferably at least 100:1, even more preferably at least 200:1.

This can be achieved by feeding a molar ratio of the alcohol to the furfuryl alcohol (combined totals from the first and second mixtures for the fed batch reactor and the continuous stirred-tank reactor embodiments) to the reaction mixture of between about 1:1 to 5:1, optionally about 1.1:1 and 3:1; further optionally between about 1.2:1 and 2.7:1; still further optionally about 2.2:1 or about 1.5:1.

The process according to the invention may be carried out as a fed-batch or continuous mode. When furfuryl alcohol is continuously fed to the first homogeneous sulfonic acid catalyst, it is preferred to supply the furfuryl alcohol at a feed rate of no more than 200 grams furfuryl alcohol per gram catalyst per hour, more preferably no more than 100 g/g/h, even more preferably no more than 50 g/g/h (grams furfuryl alcohol per gram of the catalyst in the reaction mixture per hour). In one preferred embodiment, the process is carried out in a continuously stirred tank reactor (CSTR). An advantage of such CSTR reactor is that the furfuryl alcohol that is fed into the reactor is rapidly mixed in the reaction mixture, thus avoiding a high concentration of furfuryl alcohol near the homogeneous sulfonic acid catalyst.

The process according to the invention is carried out at a first reaction temperature in the range of from 125 to 180° C., preferably in the range of from 130 to 150° C., more preferably about 140° C. The upper limit depends on the rate of forming primary (from furfuryl alcohol) and secondary byproducts (from the levulinate ester, such as Diels-Alder reactions) and to avoid excessive ether formation (unless, of course, ether formation is desired).

When the process is carried out in continuous mode, a volume that is withdrawn from the first CSTR may be supplied to a second reactor that is a second or subsequent CSTR, or a plug low reactor, hereinafter a "second reactor". The reaction temperature in the second reactor—a second reaction temperature—may be equal or higher than the first reaction temperature.

The pressure at which the reactants are contacted with the catalyst is not critical. Preferably, in order to avoid evaporation of reactants, the reactor is enclosed and the pressure is at least the autogenous pressure of the reaction mixture at the temperature at which the conversion reaction is carried out.

Preferably, the process according to the invention is a process for the conversion of furfuryl alcohol into alkyl levulinate (levulinate ester) by contacting furfuryl alcohol and an alkyl alcohol.

The alkyl alcohol preferably is an alkyl alcohol having no more than 24 carbon atoms, even more preferably selected from methanol, ethanol, isopropanol, n-propanol, n-butanol, 2-butanol, n-pentanol, 2-ethylhexan-1-ol; or is an alicyclic alcohol preferably selected from cyclohexanol-; or a combination of two or more thereof. Ethanol and n-butanol are particularly preferred.

BRIEF DESCRIPTION OF THE DRAWINGS

In FIG. 2, the furfuryl alcohol and the butanol are provided, pre-mixed in a desired ratio, in T1 and, in FIG. 3, the furfuryl alcohol and the butanol are separately fed to SM1 (Static Mixer 1) at feed ratios to achieve the desired ratio in SM1. The setup illustrated in FIG. 3 is the setup used in Example 3.

DETAILED DESCRIPTION

The drawings refer to the alcohol as butanol. However, it will be appreciated that butanol is just one example of an alcohol that may usefully be employed in practicing the present invention.

Figure 1:
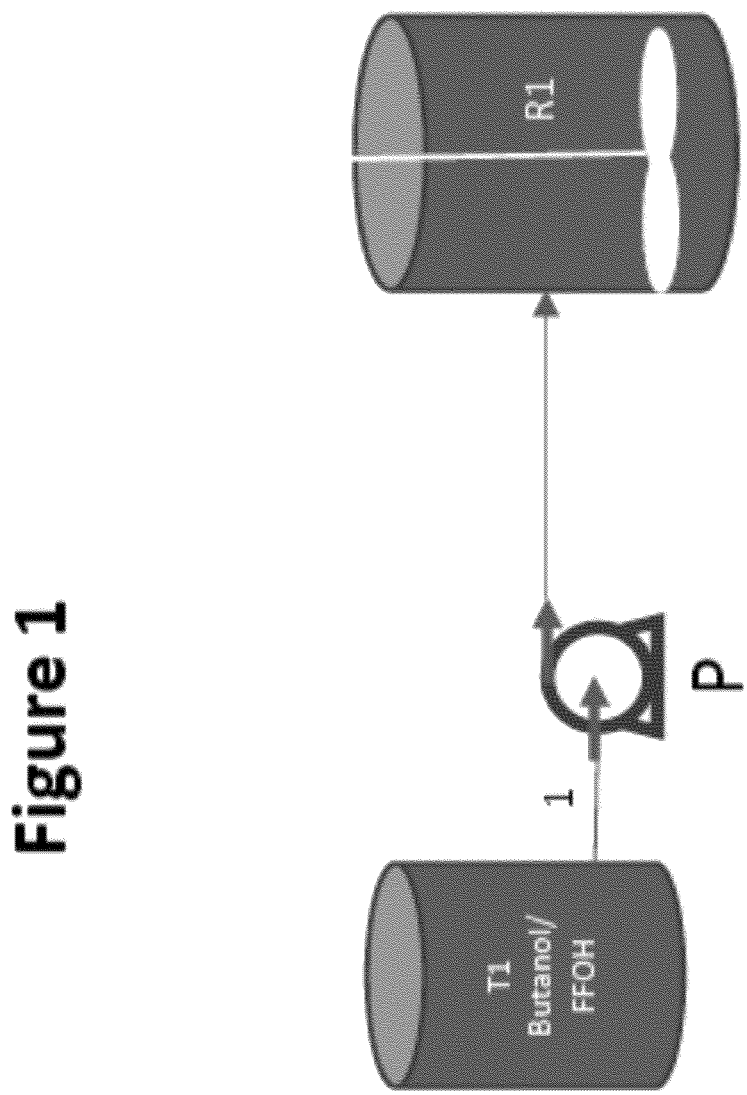
FIG. 1 shows a schematic illustration of the experimental setup concerning the fed-batch experiments, as used in Examples 1, 2 and 4.

FIG. 1 shows a schematic illustration of the experimental setup concerning the fed-batch experiments. The main elements are: (T1) the feed furfuryl alcohol/butanol tank, (P) a pump, and (R1) a stirred reactor.

Figure 2:
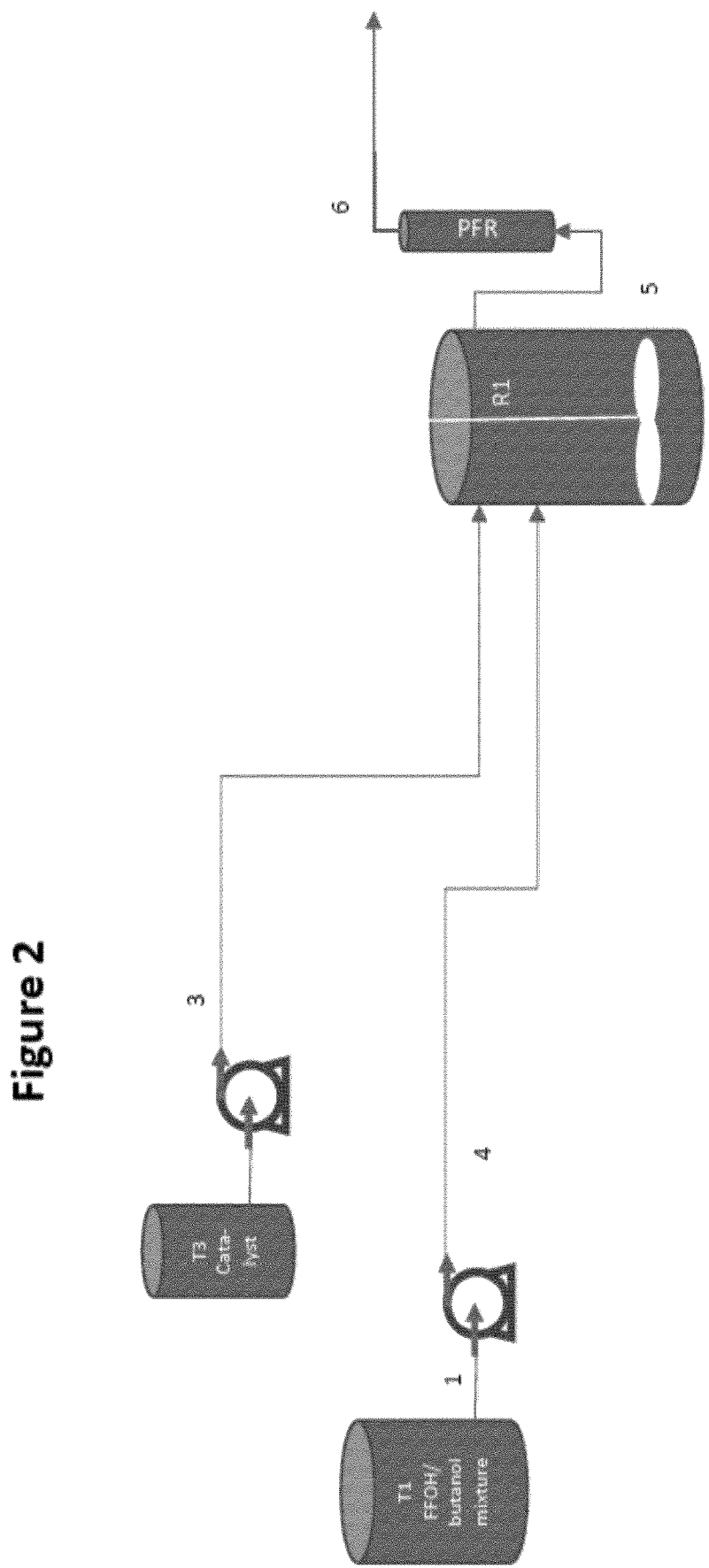
FIGS. 2 and 3 show schematic illustrations of the experimental setup for a continuous stirred tank reactor, followed by a plug flow reactor.

FIG. 2 shows a schematic illustration of a continuous stirred tank reactor. The main elements are: (T1) the feed furfuryl alcohol/butanol tank, (T3) the catalyst tank, (R1) a stirred reactor and (PFR) a plug flow reactor.

Figure 3:
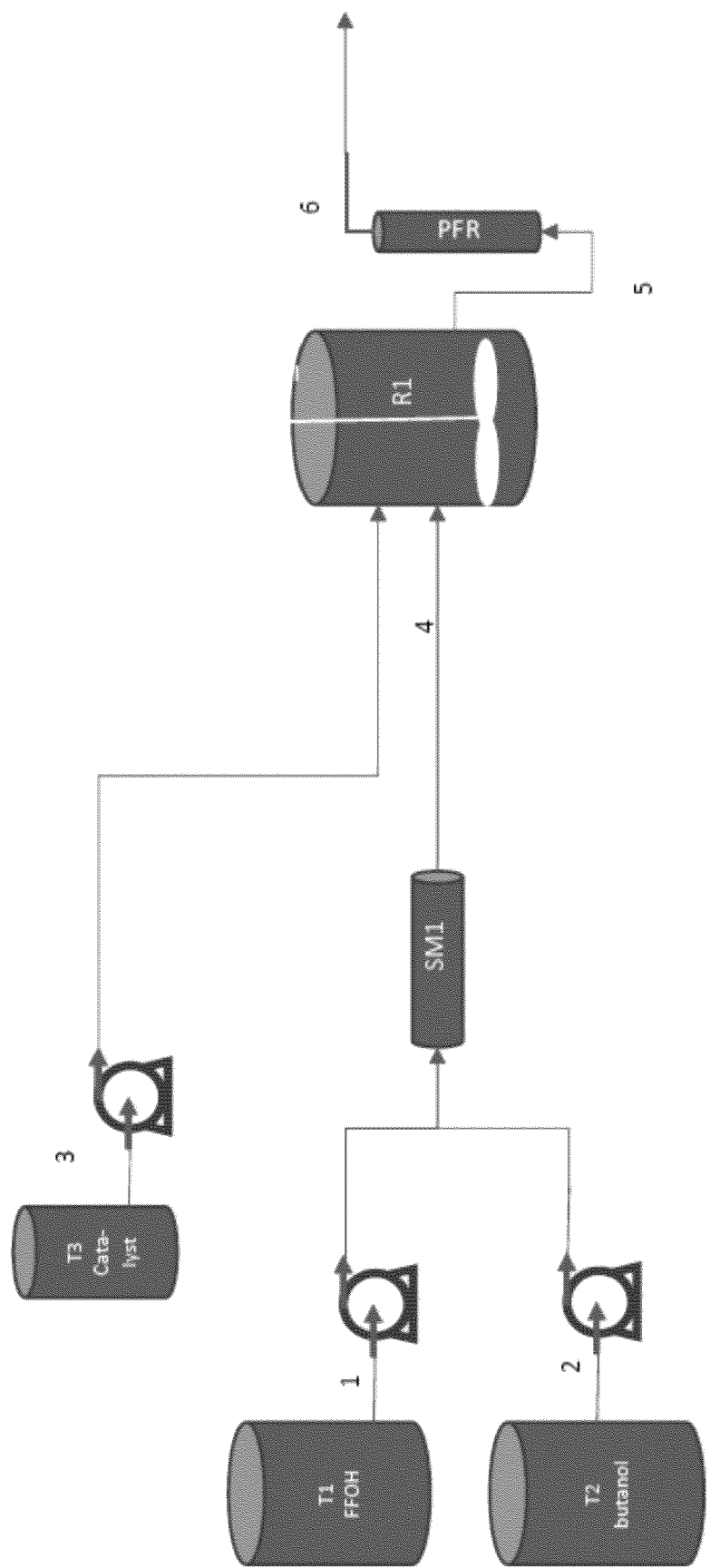

FIG. 3 shows a schematic illustration of an alternative continuous stirred tank reactor. The main elements are: (T1) the feed furfuryl alcohol tank, (T2) the feed butanol tank, (SM1) a static mixer to mix the furfuryl alcohol feed with the butanol feed, (T3) the catalyst tank, (R1) a stirred reactor and (PFR) a plug flow reactor.

Several variations are possible, described herein with reference to FIGS. 1 to 3.

Variation A: Thus, Examples 1, 2 and 4 were carried out in fed-batch mode using the experimental setup of FIG. 1. A Reactor R1 (1000 mL) was loaded with 219.14 g butanol (2.94 mol, 99.4% purity) and 0.032 mol of acid catalyst (6.05 g para-toluene sulfonic acid monohydrate (p-TSA, 99% purity). Subsequently, the butanol and catalyst were mixed (600 rpm), and the mixture was heated to 130° C. Once the reaction temperature was reached, the feeding of a mixture of butanol 205.79 g (2.76 mol, 99.4% purity) and furfuryl alcohol (FFOH) 205.54 g (2.05 mol, 98% purity) (molar ratio 1.35:1) was started via pipe 1 and pump (P). The mixture was continuously fed over a time period of 410 minutes, making sure that the furfuryl alcohol concentration in the reactor was always below 0.2 wt %. The reaction temperature of 130° C. was maintained in the reactor R1. The final overall molar ratio of butanol/furfuryl alcohol is 2.78; that of furfuryl alcohol/pTSA is 65.2 and has a weight ratio of 33.6.

After feeding is finished, the reactor (R1) is kept for 2 hours at the reaction temperature to allow the last traces of furfuryl alcohol and all intermediates are converted to butyl levulinate.

Variation A, in which the butanol and furfuryl alcohol has been pre-mixed, has been used in the examples herein, with the exception of Example 3, where Variation C has been used.

Variation B (see FIG. 2) is similar to Variation A. After loading the Reactor R1 with 219.14 g butanol (2.94 mol, 99.4% purity) and 0.032 mol of acid catalyst (6.05 g para-toluene sulfonic acid monohydrate (p-TSA, 99% purity—via a pump and pipe 3), the butanol and catalyst were mixed (600 rpm), and the mixture was heated to 130° C. Once the reaction temperature was reached, the feeding of a mixture of butanol 205.79 g (2.76 mol, 99.4% purity) and furfuryl alcohol (FFOH) 205.54 g (2.05 mol, 98% purity) (molar ratio 1.35:1) was started via pipe 1, a pump and pipe 4. R1 may be a fed batch reactor. Alternatively, R1, when filled, may become a continuous stirred tank reactor with optional onward feeding to the plug flow reactor (PFR).

Variation C (see FIG. 3) is also similar to Variation A. After loading the Reactor R1 with 219.14 g butanol (2.94 mol, 99.4% purity—from T2, via pipes 2 and 4 (and a pump and the static mixer (SM1) and 0.032 mol of acid catalyst (6.05 g para-toluene sulfonic acid monohydrate (p-TSA, 99% purity—from T3 via pipe 3), the butanol and catalyst were mixed (600 rpm), and the mixture was heated to 130° C. Once the reaction temperature was reached, the feeding of a mixture of butanol 205.79 g (2.76 mol, 99.4% purity) and furfuryl alcohol (FFOH) 205.54 g (2.05 mol, 98% purity) (molar ratio 1.35:1) was started via pipes 2 and 1, the static mixer 1 (SM1) and pipe 4. R1 may be a fed batch reactor. Alternatively, R1, when filled, may become a continuous stirred tank reactor with optional onward feeding to the plug flow reactor.

Variation D: This is identical to Variations A to C but, after feeding is finished, the reactor (R1) is kept for 0.5 hours at a temperature 15° C. higher than the reaction temperature to allow that the last traces of furfuryl alcohol and all intermediates are converted to butyl levulinate. That reduces the cycle time in fed-batch experiments.

Variation E: Identical to Variation A, but with the following difference, with reference to FIG. 3.

A Reactor R1 (1000 mL) was loaded with 219.14 g butanol (2.94 mol, 99.4% purity). Subsequently, the butanol and catalyst were mixed (600 rpm), and the butanol and catalyst were heated to 130° C. Once the reaction temperature was reached, the feeding of butanol 205.79 g (2.76 mol, 99.4% purity, from T2 via pipe 2) and furfuryl alcohol (from T1 via pipe 1) 205.54 g (2.05 mol, 98% purity) (molar ratio 1.35:1) started. Both are mixed in the Static Mixer SM1 and fed to the reactor R1. At the same time as the feeding of the mixture starts, feeding of 0.032 mol of acid (6.05 g para-toluene sulfonic acid monohydrate (p-TSA, 99% purity)) starts from T3 via a separate pipe 3. The mixture, as well as, the catalyst were continuously fed over a time period of 410 minutes, making sure that the furfuryl alcohol concentration in the reactor was always below 0.2 wt %. All the other conditions are identical to Variations A or B.

The final overall molar ratio of butanol/furfuryl alcohol is 2.78; and that of furfuryl alcohol/pTSA is 65.2 and has a weight ratio of 33.6.

After feeding is finished, the reactor R1 may be kept for 2 hours at the reaction temperature to allow that the last traces of furfuryl alcohol and all intermediates are converted to butyl levulinate. The advantage of Variation E is expected to be that significantly less dibutyl ether would be made.

Figure 4:
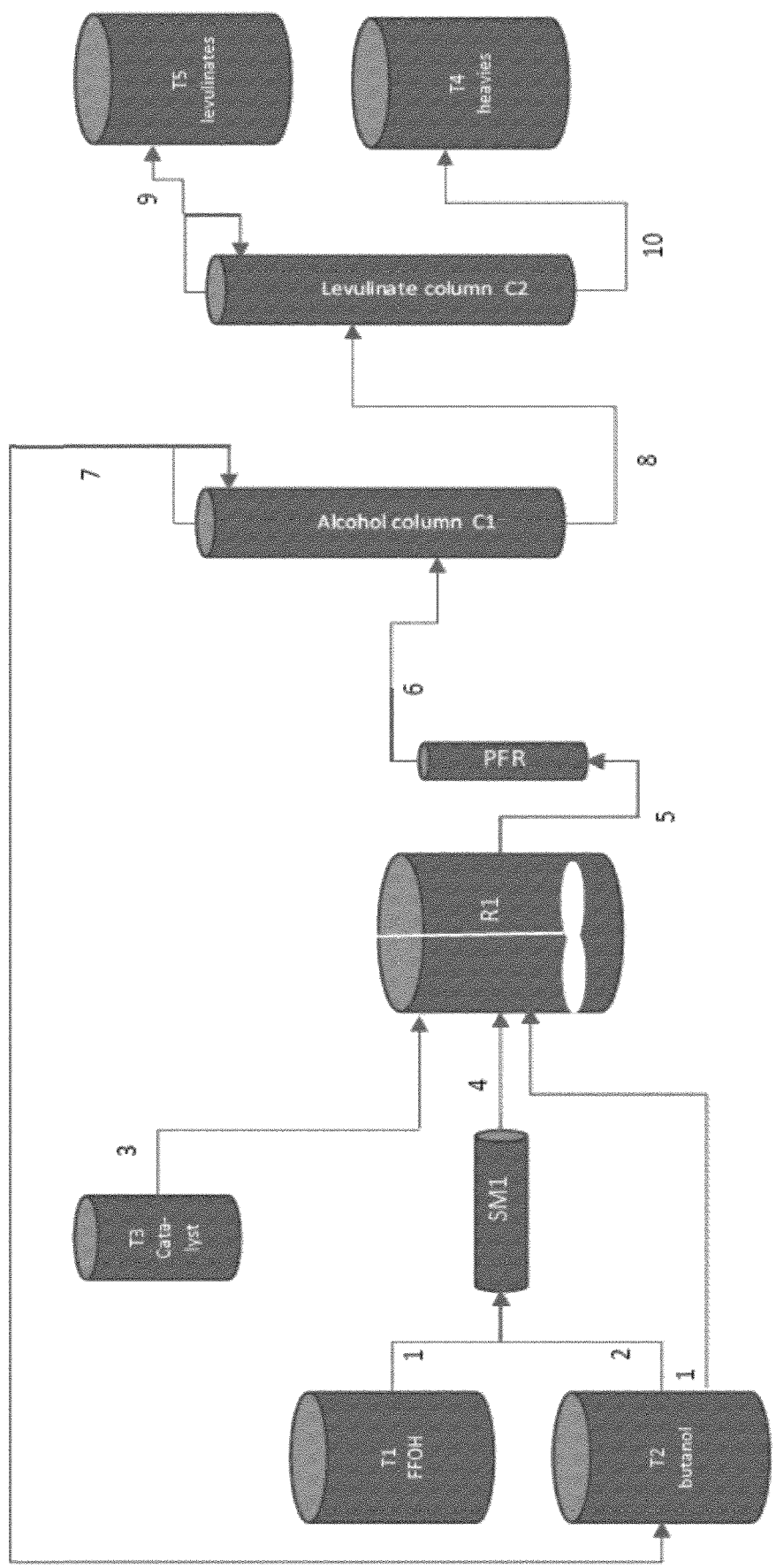
FIG. 4 shows a schematic illustration of the experimental setup of a continuous plant.

FIG. 4 shows a schematic illustration of the experimental setup of a continuous plant. The main elements are: (T1) the feed furfuryl alcohol tank, (T2) the feed butanol tank, (SM1) a static mixer to mix the furfuryl alcohol feed with the butanol feed, (T3) the catalyst tank, and (R1) a Continuous Stirred Tank Reactor (CSTR). R1 is connected with a Plug Flow Reactor (PFR), which is essentially a long pipe. The PFR is connected with an alcohol distillation column (C1)—the top can be recycled via pipe 7 to T2, the butanol tank, and the bottom is fed, via pipe 8, to C2, a levulinate column, from the top of which levulinate esters are collected in T5 and, from the bottom of which, heavies are collected in T4.

The start-up of the continuous mode reaction is identical as the fed-batch described in relation to FIG. 1 and the mode of operation can be each of the Variations A to E. Once the reactor R1 is filled, the reactor (R1) starts to work as a CSTR reactor. That is, continuously a mixture of furfuryl alcohol and butanol in a molar ratio of, for example, 1.3 is fed to R1 and via a separate pipe continuously the catalyst, pTSA, optionally dissolved in the alcohol such as butanol, is fed, at the same time, to R1, such that the concentration of pTSA in the reactor R1 is maintained at 1 wt % and, at the same time, the same volume as both streams together is removed from the stirred reactor R1 via pipe 5 to the plug flow reactor (PFR). In the CSTR R1, the residence time is sufficiently long that furfuryl alcohol is converted at more than 99%. At 140° C., that is 2.4 hour (144 minutes). The final less than 1% of furfuryl alcohol and intermediates to butyl levulinate are all converted in the plug flow reactor (PFR) in a residence time of 30 minutes at 140° C. The stream then goes on to a distillation column C1, as described above.

Definitions

A "heterogeneous catalyst" is a solid catalyst and therefore in a phase different from the reaction mixture which is a liquid phase. In contrast, homogeneous catalysts are soluble in the reaction mixture and therefore homogeneous catalysis refers to reactions where the catalyst is in the same phase as the reactants, principally in solution. Herein, the reaction mixture is liquid and the catalyst is dissolved in the liquid reaction phase.

As used herein, the "selectivity" of the levulinate ester product is calculated using the following equation:

Selectivity (mol %)=(moles of alkyl levulinate at the end of the reaction/(moles of furfuryl alcohol fed to the reactor-moles of furfuryl alcohol at the end of the reaction) in mol %

Thus, when there is 100% conversion, no unreacted furfuryl alcohol remains in the reaction mixture at the end of the reaction.

A "sulfonic acid catalyst" is a homogeneous catalyst. However, a "sulfonic acid catalyst", as used herein, may be a hydrate but is not a salt. Specifically, a "sulfonic acid catalyst" excludes salts such as sulfonic acid-functionalised ionic liquids.

"Strong protic acids" are defined as protonated acids having a dissociation constant, or Ka, value of at least about 55 at 25° C./1 atm pressure. "Weak protic acids" are defined as protonated acids having a Ka value of less than 55.

Sulfonic acids, $RSO_2OH$, feature a tetrahedral sulfur centre, meaning that sulfur is at the center of four atoms: three oxygens and one carbon. p-Toluenesulfonic acid and methanesulfonic acid have pKa values of −2.8 and −1.9, respectively. However, as a consequence of their strong acidity, their pKa values cannot be measured directly, and values commonly quoted should be regarded as indirect estimates with significant uncertainties. For instance, various sources have reported the pKa of methanesulfonic acid to be as high as −0.6 or as low as −6.5.

Strong acids have a pKa <−1.74, so p-TSA is a strong acid. It will be appreciated that a Ka of 10 is equal to a pKa of −1 and a Ka of 55 is equal to a pKa of −1.74 because it is a −log scale.

Catalyst performance is measured in terms of activity, conversion, selectivity, and productivity and, in the case of expensive and/or heterogeneous catalysts, also catalyst life time. Activity is the amount of substrate which can be converted per amount of catalyst and time unit and is in direct relation with productivity, which is the amount of product produced per unit of volume and per unit of time. A low activity can be compensated with an increased amount of catalyst but that goes with higher catalyst costs. A high selectivity is important as a low selectivity implies wasted raw materials and the need for costly, energy-intensive product separations. A high conversion is required to minimise or avoid separation costs for recycling the starting material. If the catalyst is expensive, which is often the case for a heterogeneous catalyst, or for homogenous catalysts with precious metals then catalyst lifetime and recycling is important to be economical competitive. Instead of life time a better measurement is the amount of product made under industrial conditions per amount of catalyst.

EXAMPLES

Materials

All chemicals were purchased from Sigma Aldrich.

Analytical Methods

GC-Analysis

Product concentrations were analyzed by a gas chromatography equipped with flame ionization detector (GC-FID). The GC-FID analysis was performed with a Capillary column: Column-Restek Rxi-5 ms, 30 meters, 0.25 mm ID. 0.25 μm film thickness and, as conditions, the following was used:

A He flow of 1.5 mL/min;
Start at 40° C. and keep it for 2 min at that temperature;
Increase temperature with 20° C./min up to 300° C. and hold it for 5 min at that temperature;
The FID was at 300° C.; and 1,2,4-Trimethylbenzene was used as internal standard for the GC.

Sample Preparation Procedure i. 150-300 mg of sample weighed, and 3 g of MTBE solvent is added, weight recorded, filtered, and run on the GC.
ii. Quantification is via an external calibration curve. Several concentrations (typically 5) of each component of interest are made up in MTBE between 5 and 50 mg/g. These are run on the GC and the area counts for each component are integrated and a calibration curve is generated by the GC software.
iii. The calibration curve is then used to quantify components in the unknown sample by entering the weight of the GC preparation, and then a weight % of each component is generated for each component found in the chromatogram.
iv The instrument calibration accuracy is checked, and the results are adjusted as needed by running a known purity butyl levulinate check sample, one for every 5 samples in the queue.

Product yields and selectivities are calculated from their amount compared to the amount of reference standard and corrected with the correction factors experimentally determined for the dialkyl ether, the alkanol, furfuryl alcohol and alkyl levulinate.

Correction factors of the intermediates and heavies are estimated, based on their O/C ratio (oxygen over carbon ratio because that has a major influence on the sensitivity of the FID (Flame Ionization Detector) or their expected O/C ratio for unknown compounds.

Water Analysis

The water content is analysed via the Karl Fisher method (ASTM E203—16: Standard Test Method for Water Using Volumetric Karl Fischer Titration) on a Mettler Toledo DL31 instrument.

The process of the present invention is further illustrated by means of the following non-limiting examples.

Example 1A and Comparative Example 1B

Fed-Batch Experiment

FIG. 1 shows a schematic illustration of the experimental setup concerning the fed-batch experiments. The main elements are: (T1) butanol/furfuryl alcohol feed vessel, (R1) reactor, (P) a pump device, for example, a pump from Scientific Systems, Inc. HPLC-style piston pump Series 1, 0-10 ml/min.

Example 1A was carried out in fed-batch mode using the experimental setup of FIG. 1.

219.14 g butanol (2.94 mol, 99.4% purity) and 0.032 mol of acid sites (or protons) (6.05 g para-toluene sulfonic acid monohydrate (p-TSA, 99% purity)) were manually added to reactor R1 (1000 mL). The reactor was closed and flushed for 5 minutes with nitrogen to remove most of the air (to reduce oxidation side reactions) and to reduce the contribution of atmospheric humidity to the conditions within the reactor. Then the mixture was heated to 130° C. and the pressure was the autogenic pressure which is about 2 bar. A mixture of butanol 205.79 g (2.76 mol, 99.4% purity) and furfuryl alcohol 205.54 g (2.05 mol, 98% purity) (molar ratio 1.35:1) are slowly and continuously fed over 410 minutes time to the reactor (1000 mL) (4.97 grams furfuryl alcohol per gram of the catalyst in the reaction mixture per hour or 940 g furfuryl alcohol per mol of catalyst and per hour). The overall molar ratio of butanol/furfuryl alcohol in the reaction mixture is 2.78. The molar ratio of furfuryl alcohol/pTSA is 65.2 and weight ratio is 33.6 (both referring to the reaction mixture). The total weight of the reaction mixture is 636.52 g and the catalyst is 0.95 wt % in the reaction mixture. The sulfonic acid catalyst comprises about 0.95% (w/w) of the reaction mixture.

Comparative Example 1B was also carried out in fed-batch mode using the experimental setup of FIG. 1.

218.23 g butanol (2.93 mol, 99.4% purity) and 0.032 mol of acid sites (or protons) (3.156 g sulfuric acid 98% purity) were manually added to reactor R1 (1000 ml). The reactor was closed and flushed for 5 minutes with nitrogen to remove most of the air (both oxygen and humidity). Then the mixture was heated to 130° C. and the pressure was the autogenic pressure which is about 2 bar. A mixture of butanol 202.44 g (2.71 mol, 99.4% purity) and furfuryl alcohol 205.44 g (2.05 mol, 98% purity) (molar ratio 1.32:1) is slowly and continuously fed over 410 minutes time (this feeding time of 410 minutes is referred as about 7 hours in Example 3) to the reactor R1 (1000 mL) (9.52 grams furfuryl alcohol per gram of the catalyst in the reaction mixture per hour or 940 g furfuryl alcohol per mol of catalyst and per hour). Overall molar ratio of butanol/furfuryl alcohol in the reaction mixture is 2.75. The molar ratio of furfuryl alcohol/sulfuric acid is 65.1 and weight ratio is also 65.1 as they have the same molecular weight (both referring to the reaction mixture).

For each of Example 1A and comparative Example 1B, the alcohol and acid catalyst were initially fed into the reactor R1 at room temperature. The reactor R1 was closed, and the air was replaced by nitrogen flushing. Then, the mixture was heated until reaction temperature (130° C. for both of Example 1A and comparative Example 1B) was reached. Once the reaction temperature of 130° C. was reached, the furfuryl alcohol/butanol mixture was fed to the reactor R1 which was stirring at 600 rpm over a period of time of 410 minutes; the reaction temperature of 130° C. was also maintained. Once the feeding was finished, the reaction continued for 1 hour at the given reaction temperature of 130° C. Then the reactor R1 was cooled, and samples were analyzed by GC-FID with internal standard. It is assumed that, under these conditions, only 1 proton of sulfuric acid dissociates so, in both reactions, are identical quantities of protons present. Both reactions have the same 940 g furfuryl alcohol per mol of catalyst per hour, that is, when only 1 proton dissociates of sulfuric acid (which is very likely), then they have the same number of acid (or proton) sites.

Results—Example 1A and Comparative Example 1B

TABLE 1

| Example | Yield Butyl levulinate (mol %) | Yield (as mol percentage butanol converted to dibutyl ether and compared to mol furfuryl alcohol initially) * dibutyl ether (mol %) | Conversion furfuryl alcohol* (mol %) |
|---|---|---|---|
| 1A | 90.84 | 0.65 | 100 |
| 1B | 84.44 | 1.97 | 100 |

* If 100 mol of furfuryl alcohol is fed and finally 10 mol of butanol is converted to dibutyl ether, then 10 mol % is converted Example 1A shows significantly lower formation of dibutyl ether compared to Comparative Example 1B and, at the same time, a higher molar conversion of furfuryl alcohol to butyl levulinate. Some traces of levulinic acid were found but, due to the small amount and tailing of the peak, it could not be integrated. The amount was, in both cases, below 0.2 wt %. All intermediates were converted after the reaction was stopped.

Selectivity for butyl levulinate product is calculated by mol of butyl levulinate/(initial mol furfuryl alcohol—mol of furfuryl alcohol at the end)*100, which is equal to yield if all furfuryl alcohol is converted at the end, which is the case in all experiments.

Example 1A shows a higher yield for butyl levulinate compared to Comparative Example 1B—90.84% vs 84.44% (Because the conversion of furfuryl alcohol is, in all experiments, 100%, the yield is equal to the selectivity).

These were surprising results because, based on prior literature (Lange et al 2009), it was expected, at a first reaction temperature of 130° C., that pTSA and sulfuric acid would give identical yields and selectivities for butyl levulinate as the same amount of protons are present and the protons are all easily accessible.

Comparative Example 2A, Comparative Example 2B and Comparative Example 2C

The experiment is done in fed-batch in an identical manner as in Example 1A and Comparative Example 1B, other than:
the reaction temperature now was 116° C.,
the time of addition was 5 hours and
on weight basis, about twice the amount of pTSA was used compared to sulfuric acid so that, on molar basis, when only 1 proton of sulfuric acid dissociates, the same amount of acidic sites are present—thus, the same amount of catalyst was used.

Comparative experiment 2A was carried out in fed-batch mode. Initially, 435.11 g butanol (5.84 mol, 99.4% purity) and 0.0708 mol of acid (13.74 g para-toluene sulfonic acid monohydrate (p-TSA, 99% purity)) were manually fed into a reactor R1 (2000 mL). The reactor was closed and flushed for 5 minutes with nitrogen to remove most of the air and humidity of the air. Then the mixture was heated to about the boiling point of butanol (116° C.) and the pressure was the autogenic pressure which is about 1 bar (at 116° C.). A mixture of butanol 404.03 g (5.42 mol, 99.4% purity) and furfuryl alcohol 411.34 g (4.11 mol, 98% purity) (molar ratio 1.32:1) is slowly and continuously fed over 300 minutes time to the reactor (at a feed rate of 5.99 grams furfuryl alcohol per gram of the catalyst in the reaction mixture per hour or 1162 g furfuryl alcohol per mol of catalyst and per hour). The overall molar ratio of butanol/furfuryl alcohol is 2.74 in the reaction mixture. The molar ratio of furfuryl alcohol/pTSA is 58.04 and weight ratio is 29.93 (both referring to the reaction mixture).

Comparative experiment 2B was also carried out in fed-batch mode. 435.9 g butanol (5.55 mol, 99.4% purity) and 0.063 mol of acid (6.28 g sulfuric acid 98% purity)) were fed to the reactor (2000 mL). The reactor was closed and flushed for 5 minutes with nitrogen to remove most of the air and humidity of the air. Then the mixture was heated to 116° C. and the pressure was the autogenic pressure which is about 1 bar (at 116° C.). A mixture of butanol 404.01 g (5.14 mol, 99.4% purity) and furfuryl alcohol 412.17 g (4.12 mol, 98% purity) (molar ratio 1.25:1) is slowly fed, over 5 hours to the reactor (2000 mL) (at a feed rate of 13.13 grams furfuryl alcohol per gram of the catalyst in the reaction mixture per hour or 1308 g furfuryl alcohol per mol of catalyst and per hour). The overall molar ratio of butanol/furfuryl alcohol is 2.60 in the reaction mixture. The molar ratio of furfuryl alcohol/sulfuric acid is 65.66 and weight ratio is 65.66 (both referring to the reaction mixture).

Comparative experiment 2C was also carried out in fed-batch mode. 435.65 g butanol (5.54 mol, 99.4% purity) and 0.063 mol of acid (6.26 g sulfuric acid 98% purity)) were fed to the reactor (2000 mL). The reactor was closed and flushed for 5 minutes with nitrogen to remove most of the air and humidity of the air. Then the mixture was heated to 116° C. and the pressure was the autogenic pressure which is about 1 bar (at 116° C.). A mixture of butanol 404.74 g (5.15 mol, 99.4% purity) and furfuryl alcohol 412.5 g (4.12 mol, 98% purity) (molar ratio 1.25:1) is slowly fed over 5 hours to the reactor (2000 mL) (at a feed rate of 13.18 grams furfuryl alcohol per gram of the catalyst in the reaction mixture per hour or 1310 g furfuryl alcohol per mol of catalyst and per hour). The overall molar ratio of butanol/furfuryl alcohol is 2.60 in the reaction mixture. The molar ratio of furfuryl alcohol/sulfuric acid is 65.88 and weight ratio is 65.88 (both referring to the reaction mixture).

Initially, the alcohol and acid catalyst were manually fed into the reactor at room temperature. The reactor was closed, and the air was replaced by nitrogen flushing. Then this mixture was heated until reaction temperature was reached. Once reaction temperature was reached, the furfuryl alcohol/butanol mixture was fed to the reactor which was stirring at 600 rpm over a period of time of 300 minutes (5 hours) while maintaining the reaction temperature. Once the feeding was finished, the reaction continued for 1 hour at the given reaction temperature. Then the reactor was cooled, and samples were analyzed by GC-FID with internal standard. It is assumed that, under those conditions, only 1 proton of sulfuric acid dissociates, so there are slightly more protons with pTSA, but sulfuric acid is a stronger acid.

Comparative Experiments 2B and 2C have been included to show that, under almost identical reaction conditions, the results show a similar effect.

Results—Comparative Example 2A and Comparative Examples 2B and 2C

TABLE 2

| Example | Yield Butyl levulinate (mol %) | mol of butanol converted to dibutyl ether expressed as moles butanol and based on moles of initial furfuryl alcohol* (mol %) |
|---|---|---|
| 2A | 76.67 | 0.55 |
| 2B | 86.07 | 2.29 |
| 2C | 86.32 | 2.15 |

*If 100 mol of furfuryl alcohol is fed and finally 10 mol of butanol is converted to dibutyl ether then 10 mol % is converted Comparative Example 2A shows a significantly lower formation of dibutyl ether compared to Comparative Examples 2B and 2C. However, the yield of butyl levulinate is also lower for Comparative Example 2A, compared to Comparative Examples 2B and 2C. All intermediates were converted after the reaction was stopped.

So, at lower temperatures, sulfuric acid was more selective than pTSA as a catalyst, even with a slightly higher molar amount of protons in the reaction with pTSA.

Comparative Example 2A shows that 116° C. is too low a temperature for the reaction with pTSA (compare with Example 1A).

In contrast, sulfuric acid was more selective at 1160° C. than at 130° C. (see Comparative Example 1B).

The influence of temperature is different for sulfuric acid than for pTSA, which was not expected.

Example 3A to 3G

In Examples 3A to 3G, reaction conditions (pTSA concentration, butanol/furfuryl alcohol ratio in feed and in overall reaction mixture, and the temperature) are varied, following the procedure of Example 1A (1 L reactor). The experimental setup of FIG. 1 is used, by placing the desired molar ratio of butanol/furfuryl alcohol into T1. Alternatively, the experimental set is that of FIG. 3, permitting, for Example 3F, the feed of the furfuryl alcohol and of the butanol to be independently varied.

Results—Example 3A to 3G

TABLE 3

| Example | pTSA (wt %) | Feed Butanol/ furfuryl alcohol (mol/mol) | Total Butanol/ furfuryl alcohol (mol/mol) | Feeding time (hour) | After feeding Time (minutes) | Temperature (° C.) | Yield Butyl levulinate (mol %) | mol of butanol converted to dibutyl ether based on moles of initial furfuryl alcohol* (mol %) |
|---|---|---|---|---|---|---|---|---|
| 3A | 1 | 1.3:1 | 2.7:1 | 7 | 120 | 150 | 86.19 | 15.94 |
| 3A' | 1 | 1.3:1 | 2.7:1 | 7 | 120 | 150 | 93.02 | 13.81 |
| 3B | 1 | 1.3:1 | 2.7:1 | 7 | 60 | 140 | 91.72 | 6.36 |
| 1A | 1 | 1.3:1 | 2.7:1 | about 7 | 60 | 130 | 90.84 | 3.07 |
| 3C | 1 | 1.3:1 | 2.7:1 | 10 | 120 | 140 | 89.01 | 10.79 |
| 3D | 1 | 1.3:1 | 2.7:1 | 4 | 120 | 140 | 84.31 | 5.23 |
| 3E | 1 | 1.3:1 | 2.2:1 | 7 | 120 | 140 | 90.4 | 6.45 |
| 3F | 1 | 0.8:1 | 2.2:1 | 7 | 120 | 140 | 90.0 | 6.92 |
| 3G | 0.5 | 1.3:1 | 2.7:1 | 7 | 120 | 140 | 88.89 | 4.46 |
| 3H | 0.5 | 1.3:1 | 2.7:1 | 7 | 120 | 160 | 93.4 | 24.7 |
| 3I | 1 | 1.3:1 | 2.7:1 | 7 | 120 | 125 | 92.45 | 2.95 |
| 3J | 1 | 1.3:1 | 2.7:1 | 7 | 120 | 170 | 89.21 | 39.28 |

*If 100 mol of furfuryl alcohol is fed and finally 10 mol of butanol is converted to dibutyl ether then 10 mol % is converted Example 3A' is a reproduction of Example 3A. However, there was a calibration error in original Example 3A, so the data in Example 3A' are more representative. The data in Example 3A' show that, as the temperature rises from 140° C. (Example 3B), the butyl levulinate yield rises slightly, whilst the dibutyl ether yield doubles.

Example 3H was carried out at a temperature of 160° C. for 7 hours.

Under these lab scale conditions, Example 3B is currently optimal under these reaction conditions and has been highlighted in bold. This is because the yield of butyl levulinate (BL) rises with temperature but the dibutyl ether by-product rises much more with temperature. Thus, at 160° C., (Example 3H), the yield of butyl levulinate is good, but large amounts of dibutyl ether are made.

Examples 3B and 1A differ only in their reaction temperature. The yield and selectivity are both better at a first reaction temperature of 140° C.

Examples 3C and 3D differ only in their feeding times. The yield and selectivity are both better when the mixture of butanol and furfuryl alcohol is fed to the reactor over 10 hours, when compared with 4 hours, but the lower feeding rate enhances the amount of dibutyl ether made and the 10 hours feeding time did not improve the yield of butyl levulinate, therefore 7 hours reaction time is seen as optimum under these conditions.

Examples 3E and 3F differ in the molar ratio of butanol to furfuryl alcohol in the feed to the reactor. For each of Examples 3E and 3F, the mixture of butanol and furfuryl alcohol is fed to the reactor over 7 hours and the reactor is held at the first reaction temperature for 2 hours after the addition of the butanol and furfuryl alcohol has been completed. The yield and selectivity are slightly better when the molar ratio in the feed is 1.3:1 (butanol: furfuryl alcohol).

The examples show that a good yield is obtained at temperatures between 125 and 170° C. However, increasing the temperature increases also the dialkyl ether formation and, above 170° C., the amount of dialkyl ether formed becomes unacceptably high. Example 2 had, earlier, shown that the yield at 116° C. (Comparative Example 2A) was significantly lower. Higher temperatures increased the yield of dibutyl ether. Slower feeding of the furfuryl alcohol to the reaction mixture (Example 3C) did not increase the yield of butyl levulinate, but increased the yield of dibutyl ether. Faster feeding of the furfuryl alcohol dropped the yield (Example 3D). The dibutyl ether was lower when the furfuryl alcohol was fed faster but was higher when it was fed slower (Example 3C). If the butanol quantity was reduced compared to furfuryl alcohol, either in the feed (Example 3F) or in the reactor (Example 3E), the butyl levulinate yield was still high and the dibutyl ether did not change significantly.

Reducing the amount of catalyst by 50% did decrease the amount of butyl levulinate, but it was marginal, also the dibutyl ether was marginally reduced (Example 3G).

Examples 3I and 3J were carried out at 125° C. and 170° C., respectively. At 170° C., some butene formation starts and there is a small drop in butyl levulinate yield (when compared with Example 3H, carried out at 160° C.). However, the yield at 170° C. is still acceptable. At 125C, the butyl levulinate yield is comparable to that observed in Example 1A (carried out at 130° C.).

Example 3B is emboldened as representing optimal butyl levulinate selectivity (at 91.72%) with acceptable dibutyl ether formation (6.36%) at a reaction temperature of 140° C. using p-toluenesulfonic acid as the sulfonic acid catalyst.

Example 4

The experimental setup is that of FIG. 2. Alternatively, the experimental set is that of FIG. 3, permitting the feed of the furfuryl alcohol and of the butanol to be independently varied.

The mol/mol ratio (butanol/FFOH) as in Examples 3B to 3F, is varied as 1.5, 1.8 and 2.2, the temperature was fixed at 140° C., the catalyst concentration 1 wt % pTSA monohydrate and, as residence time for the CSTR and PFR, respectively, were used:
6.5 h with 20.8 minutes
5 h with 16.15 minutes and
3.5 h with 11.3 minutes The CSTR/PFR experiments were based on fed-batch experiments where, in addition, the temperature was varied and acid concentration. In the fed-batch, 91.72% yield (Example 3B) was reached for a reaction feeding time of 7 hours and, after that, 1 or 2 hours the reaction was continued batch to convert all intermediates to butyl levulinate. A mol/mol ratio of 2.7 was found as optimum for reaction yield. The reaction was upscaled in toll manufacturing and, there, a reactor yield close to 94% was reached.

Some CSTR-PFR experiments are also done with a residence time of 1 hour for the PFR when the residence time of the CSTR was 6.5 h.

It was found that the butyl levulinate yield increases with:
The residence time
The temperature (up to 140° C.)
The molar ratio butanol/furfurylalcohol
The pTSA concentration
For dibutyl ether, the yield is strongly dependent on:
The temperature
The molar ratio butanol/furfuryl alcohol (140C, 1 wt % pTSA·H2O, 5 h CSTR residence time)
2.2 molar ratio butanol/furfuryl alcohol gives 1.24 kg/100 kg furfuryl alcohol
1.8 molar ratio butanol/furfuryl alcohol gives 0.44 kg/100 kg furfuryl alcohol
1.5 molar ratio butanol/furfuryl alcohol gives 0.34 kg/100 kg furfuryl alcohol
pTSA concentration
weak dependent on the residence time (140C, 1 wt % pTSA·H2O, 2.2 mol/mol butanol/FFOH)
6.5 h residence time gives 1.8 kg/100 kg furfuryl alcohol
5 h residence time gives 1.24 kg/100 kg furfuryl alcohol
3.5 h residence time gives 0.94 kg/100 kg furfuryl alcohol During the feeding, the droplets of both streams should not be mixed with each other. In addition, droplets should be rapidly mixed up to molecular level in the reactor to avoid locally high concentrations of furfuryl alcohol and pTSA.

Example 5

This example exemplifies the reaction of furfuryl alcohol with ethanol to produce ethyl levulinate.

Example 5 was carried out identically as Example 1A (using the experimental setup of FIG. 1) with similar molar amounts (an ethanol/furfuryl alcohol molar ratio of 1.32:1 (feed) and 2.83:1 (total)), but with different weights, because the molecular weight of ethanol is different to that of butanol and obviously also the autogenic pressure which is now approximately 6 bar.

Dry ethanol (less than 0.2 wt % water) and p-toluenesulfonic acid (1 wt % in the final reaction mixture) were fed into the reactor at room temperature. The reactor (autoclave) was closed, and the air was replaced by nitrogen flushing. Then the mixture was heated until reaction temperature was reached. Once reaction temperature (135° C.) was reached, the furfuryl alcohol/ethanol mixture was fed to the autoclave which was stirring at 600 rpm, while maintaining the reaction temperature over a period of time of 420 minutes (7 hours; at a feed rate of approximately 5 grams furfuryl alcohol per gram of the catalyst in the reaction mixture per hour). Once the feeding was finished, the reaction continued for 1 or 2 hours (to a total of 480 minutes or 540 minutes) at the given reaction temperature. Then the reactor was cooled, and samples were analyzed by GC-FID with internal standard.

Examples 5B to 5C were carried out similarly, so with an alkanol/furfuryl alcohol molar ratio of 1.3:1 (feed) and in the final reaction mixture 2.7:1 (total), 7 hours feeding time and 2 hours after reaction (total time 540 minutes) and 1 wt % pTSA on the final reaction mixture.

Results Example 5—

TABLE 4

| Example | Temperature (° C.) | Yield alkyl levulinate) (540 min (%) | mol of alkanol converted to dialkyl ether based on moles of initial furfuryl alcohol* (mol %) |
|---|---|---|---|
| 5A- ethanol | 135 | 90.98 | 8.32* |
| 5B - ethylhexanol | 140 | 87.56** | 0.28 |
| 5C - 2-octanol | 140 | 90.79 | Not determined |

*If 100 mol of furfuryl alcohol is fed and finally 10 mol of ethanol is converted to diethyl ether then 10 mol % is converted
**from a lab experiment, BUT done without the 60 minutes after gradual addition.

2-Octanol is an example of a secondary alcohol being employed herein.

Ethylhexanol is an example of a branched alcohol being employed herein.

Example 5 shows that good yields are obtained with other alcohols such as another primary short chain alcohol (ethanol), a branched primary long chain alcohol (ethylhexanol), and a secondary alcohol (2-octanol).

Example 6

Example 6 was carried out in fed-batch mode using the experimental setup of FIG. 1. This Example compares various sulfonic acid catalysts, including methanesulfonic acid as an example of an aliphatic sulfonic acid, and camphor sulfonic acid as an example of a cycloaliphatic sulfonic acid.

This Example also compares the sulfonic acids with an ionic liquid catalyst—[BMIm-SH] [HSO4] (1-Butyl sulfonic acid, 3-methyl imidazolium sulfuric acid)—and with both tFA (trifluoroacetic acid) and Bi-TFA (bismuth triflate).

Examples 6D, 6E and 6F are comparative examples.

In all examples, 216 g butanol (2.91 mol, 99.4% purity) and 1 wt % (weight percent, ~6.25 g) based on the final total mixture of acid catalyst were manually added to reactor R1 (1000 mL). The reactor was closed and flushed for 5 minutes with nitrogen to remove most of the air (to reduce oxidation side reactions) and to reduce the contribution of atmospheric humidity to conditions within the reactor. Then, the mixture was heated to 140° C. and the pressure was the autogenic pressure. A mixture of butanol 200 g (2.71 mol, 99.4% purity) and furfuryl alcohol 206 g (2.05 mol, 98% purity) (molar ratio 1.31:1) are slowly and continuously fed over 420 minutes time to the reactor (1000 mL). The overall molar ratio of butanol/furfuryl alcohol in the reaction mixture is 2.73. After feeding is stopped, the reaction is left for 2 hours at reaction temperature and with continuous stirring and then the final samples are taken.

The catalysts used are pTSA (para-toluene sulfonic acid, CSA (Camphor sulfonic acid), MSA (methanesulfonic acid), [BMIm-SH] [HSO4] (1-Butyl sulfonic acid, 3-methyl imidazolium hydrogen sulfate ionic liquid), Bi-TFA (Bismuth triflate, Lewis acid) and tFA (trifluoroacetic acid).

| Example | catalyst (wt %) | Yield Butyl levulinate (mol %) | mol of butanol converted to dibutyl ether based on moles of initial furfuryl alcohol* (mol %) |
|---|---|---|---|
| 3B | pTSA | 91.72 | 6.37 |
| 6B** | CSA | 88.49 | 3.37 |
| 6C | MSA | 93.21 | 9.02 |
| Comparative 6D | [BMIm-SH] [HSO4] | 60.28 | 0.47 |
| Comparative 6E | Bi-TFA | 81.64 | 23.66 |
| Comparative 6F | tFA | 32.7 | 0.28 |

*Calculated on the basis of, when100 mol of furfuryl alcohol is fed and finally 10 mol of butanol is converted to dibutyl ether, then it is 10 divided by 100, or 10 mol % that is converted.
**no holding time—0 hours settling time Examples 3B, 6B and 6C show that all sulfonic acids give good yields of butyl levulinate. Methanesulfonic acid gives higher amounts of dibutyl ether, whereas camphorsulfonic acid gives lower amounts of dibutyl ether, in comparison with pTSA (albeit under different conditions for camphor sulfonic acid).

The ionic liquid, [BMIm-SH] [HSO4], purchased from Sigma Aldrich (Catalogue number: 57457-100G-F; lot number: BCCD9481) had surprising low yield (about 60%) but a very low dibutyl ether formation (0.47%) (Comparative Example 6D). These results were unexpected as Rode et al. (Single pot conversion of furfuryl alcohol to levulinic esters and γ-valerolactone in the presence of sulfonic acid functionalized ILs and metal catalysts, *Green Chem.*, 2013, 15, 2540-2547) published very high yields. The reasons for this difference are speculative. In the experimental results, it isn't disclosed whether they used standards (internal or external), so, if they did not use standards, and if they make heavies which are not visible in their GC method, the calculated yield will be overestimated. But, as said, this is speculative. Evidently, the low yield makes it economically not competitive with homogeneous sulfonic acids. Moreover, the ionic liquid is much more expensive to make and has a high viscosity (Mauro C. C. Ribeiro, High Viscosity of Imidazolium Ionic Liquids with the Hydrogen Sulfate Anion: A Raman Spectroscopy Study *J. Phys. Chem. B* 2012, 116, 24, 7281-7290) which makes them more difficult to handle.

Metal triflates were used by the group of Prof. Jerome; amongst them, bismuth triflate (a homogeneous catalyst, but not a homogeneous sulfonic acid catalyst) performed the best (U.S. Pat. No. 10,590,060; Alban Chappaz, Francois Jerome, Karine De Oliveira Vigier, Eric Muller, Jonathan Lai, Matthieu Corbet, Didier Morvan, Process for the preparation of levulinate esters, assigned to University of Poitiers). Using Bi-TFA, good yields (Comparative Example 6E, 81.6%) were observed. However, the yields using Bi-TFA were significantly below those observed with the homogenous sulfonic acids and, in addition, the yield of dibutyl ether was much higher than that observed when using the homogeneous sulfonic acids under the same conditions.

The trifluoroacetic acid (Comparative Example 6F) had low butyl levulinate yield and also low dibutyl ether formation. However, the butyl levulinate yield was too low to make it economically viable.

Example 7

This Example is for large scale production of ethylhexyl levulinate using a FIG. 1 experimental setup.

In a stainless steel feed tank, 1120 kg ethylhexanol is mixed with 720 kg furfuryl alcohol (mol ratio EH/FFA=1.3). In a 5000 l reactor, 1360 kg ethylhexanol is charged together with 30 kg para-toluenesulfonic acid. The reactor is heated to 140° C. and, when the temperature reaches 135° C., the feeding of the mixture of ethylhexanol with furfuryl alcohol is started. The mixture is fed over a time period of 7 hours after which the reactor is kept for 2 hours at 140° C. (+ or −5° C.) and then cooled down 60° C. The catalyst is neutralized with soda ash and, after batch distillation, 1465 kg ethylhexyl levulinate is recovered, which corresponds with an overall recovered yield of 87.44% (the reaction yield itself would have been higher). In addition, 33.2 kg diethylhexylether is identified, which corresponds with 3.7% ethylhexanol on molar basis compared to the molar amount of furfuryl alcohol present.

m

Example 8

Example 8 was carried out in CSTR followed by PFR mode according to FIG. 2. For that, a large batch was made for both the furfuryl alcohol and butanol mixture (T3) as well as the butanol and pTSA (4.85% solution) mixture (T1). So, during the test of 1 condition, there was no need to refill the batch tanks (T1 and T3). Obviously, with an extra pump and batch tank and a static mixer, the same experiments can be carried out in a set-up as explained in FIG. 3.

The effective volume of the CSTR was 750 ml and the volume of the plug flow reactor was 40 ml and a ½ inch tube was used for that. The reaction was started up in fed-batch mode (according to Example 1) and, once the reactor effective volume was reached, the system was switched to the CSTR-PFR mode. The samples were taken when steady state conditions were reached. The first time, the reactor volume needed to be replaced 8 times. After that, new conditions were chosen close to the previous condition, so that, when the reaction volume was replaced 3 times, a new steady state condition was reached. Once steady state condition was reached, sample points were taken with 1 residence time of the reactor as interval and, after 3 samples were taken, the average is made and noted here. If there were outliners, extra samples were taken and the outliners were skipped.

The mol/mol ratio (butanol/FFOH) (the butanol includes the butanol used to dilute the pTSA) is varied as 1.5, 1.8 and 2.2, the temperature was fixed at 140° C., the catalyst concentration 1 wt % pTSA mono hydrate.

Examples 8a to 8G

| Experiment | Residence time CSTR hr | residence time PFR min | butanol/furfuryl alcohol mol/mol | dibutyl ether Kg/100 kg furfuryl alcohol | Butyl levulinate yield % |
|---|---|---|---|---|---|
| 8A | 6.5 | 20.8 | 2.2 | 1.80 | 90.28 |
| 8B | 5 | 16.15 | 2.2 | 1.24 | 89.62 |
| 8C | 5 | 16.15 | 1.5 | 0.34 | 85.79 |
| 8D | 3.5 | 11.3 | 2.2 | 0.94 | 89.31 |
| 8E | 6.5 | 20.8 | 1.8 | 0.68 | 86.55 |

Examples 8A, 8B and 8D shows that reducing the residence time reduces the yield of butyl levulinate and the formation of dibutyl ether.

Examples 8B and 8C, as well as Examples 8A and 8E, show that decreasing the molar ratio of butanol/furfuryl alcohol reduces more strongly the yield of butyl levulinate and the formation of dibutyl ether.

The invention claimed is:

1. A process for the conversion of furfuryl alcohol into a levulinate ester, the process comprising contacting furfuryl alcohol; an alcohol, or a mixture thereof; and a homogeneous catalyst at a first reaction temperature in the range of from 125 to 180° C. to form a reaction mixture; and forming the levulinate ester in the reaction mixture, characterised in that the first homogeneous catalyst is a sulfonic acid catalyst.

2. The process of claim 1, wherein a first reaction temperature is between about 125° C. and 170° C.

3. The process of claim 1, wherein the sulfonic acid catalyst is selected from the group consisting of an alkyl-aromatic sulfonic acid, an aromatic sulfonic acid, a halosulfonic acid, and an aliphatic sulfonic acid.

4. The process of claim 1, wherein the sulfonic acid catalyst comprises about 0.1 to about 5% (w/w), of the reaction mixture; and/or wherein the molar ratio of the alcohol to the furfuryl alcohol added to the reaction mixture is between about 1:1 to 5:1; and/or wherein the furfuryl alcohol is fed into the reaction mixture at a feed rate of no more than 200 grams furfuryl alcohol per gram of the catalyst in the reaction mixture per hou.

5. The process of claim 1, wherein the alcohol is a primary or secondary alcohol selected from a C1-24 straight or branched chain alcohol; an alkoxy-alkanol; or a combination of two or more thereof.

6. The process of claim 1, wherein the alcohol is selected from an alicyclic alcohol; an unsaturated aliphatic alcohol; a glycol that is a primary alcohol; or a combination of two or more thereof.

7. The process of claim 1, wherein the alcohol is a mixture of one or more primary or secondary alcohols; and/or one or more alicyclic alcohols; and/or one or more unsaturated aliphatic alcohols; and one or more glycols.

8. The process of claim 1, the contacting is carried out in a fed batch reactor.

9. The process of claim 8, wherein the reaction mixture is formed by
providing (i) a first mixture comprising the alcohol or a mixture thereof, and, optionally, the homogeneous sulfonic acid catalyst in the fed batch reactor;
continuously or discontinuously feeding (ii) a second mixture comprising the furfuryl alcohol, and an additional amount of the alcohol or a mixture thereof to (i) the first mixture in the fed batch reactor; and
continuously or discontinuously feeding to the fed batch reactor, separately from the second mixture, a third mixture comprising either (iii) an additional amount of the homogeneous sulfonic acid catalyst if the first mixture comprises the homogeneous sulfonic acid catalyst; or the homogeneous sulfonic acid catalyst if the first mixture does not comprise the homogeneous sulfonic acid catalyst.

10. The process of claim 9, wherein the first temperature is maintained for up to about 2 hours, after mixing the second mixture with the first mixture has been completed; or, alternatively, the first temperature is raised to a second reaction temperature after mixing the second mixture with the first mixture has been completed and is optionally maintained at the second reaction temperature for between 5 and 120 minutes.

11. The process of claim 1, wherein the process is continuous and is carried out in a continuous stirred-tank reactor.

12. The process of claim 11, wherein the continuous stirred-tank reactor is filled with the reaction mixture by
providing (i) a first mixture comprising the alcohol or a mixture thereof, and, optionally, the homogeneous sulfonic acid catalyst in the reactor;
continuously or discontinuously feeding (ii) a second mixture comprising the furfuryl alcohol, and an additional amount of the alcohol or a mixture thereof to (i) the first mixture in the reactor; and
continuously or discontinuously feeding to the reactor, separately from the second mixture, a third mixture comprising either (iii) an additional amount of the homogeneous sulfonic acid catalyst if the first mixture comprises the homogeneous sulfonic acid catalyst; or the homogeneous sulfonic acid catalyst if the first mixture does not comprise the homogeneous sulfonic acid catalyst.

13. The process of claim 12, wherein the first mixture is heated to the first reaction temperature before the second mixture, and the third mixture are mixed with the first mixture.

14. The process of claim 9, wherein the sulfonic acid catalyst is selected such that the sulfonic acid catalyst comprises about 0.1 to about 5% (w/w) of the reaction mixture.

15. The process of claim 9, wherein the second mixture is added to the reaction mixture at a feed rate of no more than 200 grams furfuryl alcohol per gram of the catalyst in the reaction mixture per hour.

16. The process of claim 9, wherein the first and second mixtures comprise, in total, a molar ratio of the alcohol to the furfuryl alcohol of between about 1:1 to 5:1.

17. The process of claim 1, wherein the molar ratio of the alcohol or mixture thereof, to the furfuryl alcohol in the reaction mixture is at least 20:1.

18. The process of claim 12, wherein, when the continuous stirred-tank reactor has been filled to a desired volume, a volume of the reaction mixture is withdrawn from the continuous stirred-tank reactor; and the desired volume is replenished by continuously or discontinuously feeding the second mixture to the reactor; and, separately, continuously or discontinuously feeding the third mixture to the reactor, wherein the withdrawn volume is, optionally, fed to a second reactor that is in series with the continuous stirred-tank reactor.

19. The process of claim 18, wherein the process is carried out in the second reactor at a second reaction temperature, the second reaction temperature being the same as, or 5 to 15° C. higher than, the first reaction temperature in the continuous stirred-tank reactor; and/or the residence time in the second reactor is in the range of 5 to 120 minutes.

20. The process of claim 1, wherein the sulfonic acid catalyst is selected from p-toluenesulfonic acid, methanesulfonic acid, or 7,7-dimethyl-2-oxobicyclo [2.2.1]heptan-1-yl) methanesulfonic acid (camphor sulfonic acid).

* * * * *